United States Patent
Durrant et al.

(10) Patent No.: US 12,159,712 B2
(45) Date of Patent: Dec. 3, 2024

(54) CLINICAL DATA HANDOFF IN DEVICE MANAGEMENT AND DATA SHARING

(71) Applicant: ZOLL MEDICAL CORPORATION, Chelmsford, MA (US)

(72) Inventors: Ian Durrant, Arlington, MA (US); Gary A. Freeman, Waltham, MA (US); Andrew E. Fleischacker, Bedford, NH (US)

(73) Assignee: ZOLL Medical Corporation, Chelmsford, MA (US)

( * ) Notice: Subject to any disclaimer, the term of this patent is extended or adjusted under 35 U.S.C. 154(b) by 892 days.

(21) Appl. No.: 15/084,249

(22) Filed: Mar. 29, 2016

(65) Prior Publication Data

US 2016/0321400 A1    Nov. 3, 2016

Related U.S. Application Data

(60) Provisional application No. 62/140,400, filed on Mar. 30, 2015.

(51) Int. Cl.
*A61N 1/372* (2006.01)
*A61B 5/33* (2021.01)
(Continued)

(52) U.S. Cl.
CPC ............. *G16H 40/67* (2018.01); *A61B 5/33* (2021.01); *A61N 1/37217* (2013.01);
(Continued)

(58) Field of Classification Search
CPC .............. A61B 5/0402; A61N 1/3904; A61N 1/39044; A61N 1/37217; A61N 1/37282;
(Continued)

(56) References Cited

U.S. PATENT DOCUMENTS

| 6,083,248 A | 7/2000 | Thompson |
| 6,088,616 A | 7/2000 | Olson et al. |

(Continued)

FOREIGN PATENT DOCUMENTS

| JP | 2013542814 | 11/2013 |
| WO | WO-2007058835 A2 | 5/2007 |

(Continued)

OTHER PUBLICATIONS

S. Pavlopoulos, E. Kyriacou, A. Berler, S. Dembeyiotis and D. Koutsouris, "A novel emergency telemedicine system based on wireless communication technology—Ambulance," in IEEE Transactions on Information Technology in Biomedicine, vol. 2, No. 4, pp. 261-267, Dec. 1998, doi: 10.1109/4233.737581. (Year: 1998).*

(Continued)

*Primary Examiner* — Wenren Chen
(74) *Attorney, Agent, or Firm* — Finch & Maloney PLLC

(57) ABSTRACT

Aspects of the present disclosure are directed toward systems, methods an apparatuses for hand off of clinical data during a medical event. Certain embodiments of the present disclosure include a first medical device configured to, during a first part of a medical event, monitor a patient and store clinical information and a second medical device. A second medical device may display at least some of the clinical information, modify operation of the second medical device, or store the clinical information.

25 Claims, 8 Drawing Sheets

(51) Int. Cl.
*A61N 1/39* (2006.01)
*G08B 3/00* (2006.01)
*G08B 5/00* (2006.01)
*G16H 10/60* (2018.01)
*G16H 40/20* (2018.01)
*G16H 40/63* (2018.01)
*G16H 40/67* (2018.01)
*G16Z 99/00* (2019.01)
*H04W 84/12* (2009.01)

(52) U.S. Cl.
CPC ....... *A61N 1/37282* (2013.01); *A61N 1/3904* (2017.08); *A61N 1/39044* (2017.08); *A61N 1/3993* (2013.01); *G16H 10/60* (2018.01); *G16H 40/63* (2018.01); *G16Z 99/00* (2019.02); *G08B 3/00* (2013.01); *G08B 5/00* (2013.01); *G16H 40/20* (2018.01); *H04W 84/12* (2013.01)

(58) Field of Classification Search
CPC ...... A61N 1/3993; G16H 10/60; G16H 40/63; G06F 19/00; G06F 19/3418; G08B 3/00; G08B 5/00; H04W 84/12
USPC .............................................................. 705/3
See application file for complete search history.

(56) References Cited

U.S. PATENT DOCUMENTS

| | | |
|---|---|---|
| 6,363,282 B1 | 3/2002 | Nichols et al. |
| 6,370,428 B1 | 4/2002 | Snyder et al. |
| 6,397,104 B1 | 5/2002 | Miller et al. |
| 6,492,581 B1 | 12/2002 | Bradbury |
| 6,747,556 B2 | 6/2004 | Medema et al. |
| 6,754,526 B2 | 6/2004 | Daynes et al. |
| 6,813,517 B2 | 11/2004 | Daynes et al. |
| 6,937,150 B2 | 8/2005 | Medema et al. |
| 7,672,720 B2 | 3/2010 | Heath |
| 7,769,465 B2 | 8/2010 | Matos |
| 7,805,190 B2 | 9/2010 | Chapman et al. |
| 7,937,146 B2 | 5/2011 | Banville et al. |
| 7,979,378 B2 | 7/2011 | West et al. |
| 8,081,071 B1 | 12/2011 | Vaisnys et al. |
| 8,781,577 B2 | 7/2014 | Freeman |
| 8,880,166 B2 | 11/2014 | Tan et al. |
| 9,119,971 B2 | 9/2015 | Elghazzawi |
| 9,220,912 B2 | 12/2015 | Elghazzawi |
| 2001/0016696 A1 | 8/2001 | Bystrom et al. |
| 2003/0025602 A1 | 2/2003 | Medema et al. |
| 2003/0028219 A1 | 2/2003 | Powers et al. |
| 2003/0212311 A1 | 11/2003 | Nova et al. |
| 2003/0212438 A1 | 11/2003 | Nova et al. |
| 2004/0049233 A1 | 3/2004 | Edwards |
| 2004/0064342 A1 | 4/2004 | Browne et al. |
| 2004/0214148 A1 | 10/2004 | Salvino et al. |
| 2005/0015115 A1 | 1/2005 | Sullivan et al. |
| 2006/0030891 A1 | 2/2006 | Saltzstein et al. |
| 2006/0083785 A1 | 4/2006 | Kerrish et al. |
| 2006/0084043 A1 | 4/2006 | Weaver et al. |
| 2006/0149321 A1 | 7/2006 | Merry et al. |
| 2007/0032830 A1 | 2/2007 | Bowers |
| 2007/0108274 A1 | 5/2007 | Boardman et al. |
| 2007/0185545 A1 | 8/2007 | Duke |
| 2008/0097550 A1 | 4/2008 | Dicks et al. |
| 2008/0097909 A1 | 4/2008 | Dicks et al. |
| 2008/0138778 A1 | 6/2008 | Eggert et al. |
| 2008/0244717 A1* | 10/2008 | Jelatis ................ A61N 1/37254 726/5 |
| 2009/0222539 A1 | 9/2009 | Lewis et al. |
| 2010/0250643 A1 | 9/2010 | Savage et al. |
| 2010/0318143 A1* | 12/2010 | Chapman ................ G07C 9/25 607/5 |
| 2011/0057082 A1 | 3/2011 | West |
| 2011/0060378 A1 | 3/2011 | Tuysserkani |
| 2011/0284004 A1 | 11/2011 | Silver et al. |
| 2011/0295078 A1 | 12/2011 | Reid et al. |
| 2012/0081230 A1 | 4/2012 | Sullivan et al. |
| 2013/0132465 A1 | 5/2013 | Brown |
| 2014/0005736 A1* | 1/2014 | Geheb .................... A61B 5/318 607/7 |
| 2014/0365175 A1* | 12/2014 | Packer ................. A61B 5/0006 702/182 |
| 2015/0242812 A1* | 8/2015 | Nelson .................. G06Q 50/18 705/311 |

FOREIGN PATENT DOCUMENTS

| | | |
|---|---|---|
| WO | WO-2007089225 A1 | 8/2007 |
| WO | WO-2009136259 A2 | 11/2009 |

OTHER PUBLICATIONS

Hagihara A, Hasegawa M, Abe T, Nagata T, Nabeshima Y. Physician presence in an ambulance car is associated with increased survival in out-of-hospital cardiac arrest: a prospective cohort analysis. PLoS One. Jan. 8, 2014;9(1):e84424. doi: 10.1371/journal.pone. 0084424. PMID: 24416232; PMCID: PMC3885569. (Year: 2014).*

S. Son, K. Lee, D. Won and S. Kim, "U-healthcare system protecting privacy based on cloaker," 2010 IEEE International Conference on Bioinformatics and Biomedicine Workshops (BIBMW), Hong Kong, China, 2010, pp. 417-423, doi: 10.1109/BIBMW.2010. 5703838. (Year: 2010).*

International Search Report and Written Opinion issued by the U.S. Patent and Trademark Office as International Searching Authority for International Application No. PCT/US13/43274, dated Aug. 30, 2013 (7 pages).

International Search Report and Written Opinion issued by the U.S. Patent and Trademark Office as International Searching Authority for International Application No. PCT/US16/24790 dated Jun. 30, 2016 (13 pages).

International Search Report and Written Opinion issued by the U.S. Patent and Trademark Office as Searching Authority in International Application No. PCT/US16/24775, dated Jul. 1, 2016 (14 pages).

Notice of Reasons for Refusal for Japanese Patent Application No. 2017-550185, with English translation, dated Mar. 3, 2020, 10 pages.

* cited by examiner

CLINICAL DATA HANDOFF IN DEVICE MANAGEMENT AND DATA SHARING

CROSS-REFERENCE TO RELATED APPLICATIONS

This application claims the benefit of U.S. Provisional Patent Application Ser. No. 62/140,400, filed on Mar. 30, 2015, which is incorporated herein by reference in its entirety for all purposes.

TECHNICAL FIELD

Embodiments of the present disclosure relate generally to data management and sharing among medical devices.

BACKGROUND

Multiple medical devices may be used in medical situations (for example, emergent situations). These devices can be used by different personnel. For example, automated external defibrillators (AEDs) may be used by non-trained medical device personnel such as a first responder. Additionally, emergency medical technicians (EMT) may use different and additional devices in responding to an emergent situation, which may differ from devices used at a hospital. Communicating between these devices may benefit efficient and proper care of a victim in an emergent situation, as well as drive responder actions and protocol.

SUMMARY

Example 1. A system for clinical data handoff in a medical event according to an embodiment of the present disclosure includes a server device communicatively coupled to a network, the server device comprising a memory and a processor communicably coupled to the memory, the memory including instructions that, when executed by the processor, cause the processor to initiate at least one component, the at least one component comprising: a communication component configured to facilitate communication with a first medical device and a second medical device during a medical event, receive first clinical information from the first medical device, and to conduct, on the second medical device during the medical event, one or more of: (a) displaying at least some of the first clinical information on the second medical device, (b) displaying on the second medical device information derived from at least some of the first clinical information, (c) modifying operation of the second medical device based on the first clinical information, and (d) storing the first clinical information in the second medical device or a remote database; and a graphical user interface (GUI) configured to facilitate interaction between a user and the communication component.

Example 2. The system of Example 1, further comprising a wireless local area network (WLAN), and wherein the first and second medical devices are communicably coupled via the WLAN.

Example 3. The system of any of Examples 1 to 2, wherein one of the first and second medical devices also provides communications via the WLAN.

Example 4. The system of any of Examples 1 to 3, wherein the one of the first and second medical devices is also the server device.

Example 5. The system of any of Examples 1 to 4, wherein the one of the first and second medical devices is also a communications router on the WLAN.

Example 6. The system of any of Examples 1 to 5, wherein one of the first and second medical devices is a portable computing device displaying medical information.

Example 7. The system of any of Examples 1 to 6, wherein the portable computing device is an iPad®, mobile phone, smart phone, or iWatch®.

Example 8. The system of any of Examples 1 to 7, wherein at least one of the first and second medical devices is bodily-attached.

Example 9. The system of any of Examples 1 to 8, wherein the WLAN is dynamically reconfigurable and secure.

Example 10. The system of any of Examples 1 to 9, wherein the first clinical information details administration of cardiopulmonary resuscitation (CPR) to a patient during the medical event.

Example 11. The system of any of Examples 1 to 10, wherein the information derived from at least some of the first clinical information includes an indication of CPR quality.

Example 12. The system of any of Examples 1 to 11, wherein the indication of CPR quality includes an indication of chest compression metrics.

Example 13. The system of any of Examples 1 to 12, wherein the information derived from at least some of the first clinical information includes an indication of CPR time.

Example 14. The system of any of Examples 1 to 13, wherein the indication of CPR time includes one or more of: beginning time of CPR administration, ending time of CPR administration, duration of CPR administration, and chest compression timing.

Example 15. The system of any of Examples 1 to 14, wherein the first clinical information includes a patient ECG observed prior to the patient entering cardiac arrest.

Example 16. The system of any of Examples 1 to 15, wherein the first clinical information includes a patient ECG observed after a shock is administered to the patient by the first medical device.

Example 17. The system of any of Examples 1 to 16, wherein the communication component is further configured to facilitate communication with the first medical device and the second medical device in response to determining the first medical device and the second medical device are proximately located.

Example 18. The system of any of Examples 1 to 17, wherein the communication component is further configured to prompt for confirmation on either or both of the first and second medical devices, and wherein the prompt includes at least one of a key-code, a visual beacon, a visual light, an audible prompt, and a patient specific input.

Example 19. The system of any of Examples 1 to 18, wherein the communication component is further configured to determine the first medical device and the second medical device are proximately located in response to exchange of radio frequency signals.

Example 20. The system of any of Examples 1 to 19, wherein the communication component is further configured to determine the first medical device and the second medical device are proximately located in response a receipt of a global positioning system (GPS) signal from each of the first medical device and the second medical device.

Example 21. The system of any of Examples 1 to 20, wherein the communication component is further configured to determine the first medical device and the second medical device are proximately located in response to each of the first medical device and the second medical device being connected to a shared local area network (LAN).

Example 22. The system of any of Examples 1 to 21, wherein the communication component is further configured to facilitate communication with the first medical device and the second medical device in response to determining a correlation between the first clinical information and information about one or a combination of the following: an identity of a patient treated with the second medical device, a location of the patient or the second medical device, a time, an identity of a caregiver, and second clinical information gathered by the second medical device.

Example 23. The system of any of Examples 1 to 22, wherein the medical event is an emergency medical event.

Example 24. A system for hand off of clinical data (e.g. in a medical event) according to an embodiment of the present disclosure includes a first medical device configured to, during a first part of a medical event, monitor a patient and store first clinical information; a second medical device, the second medical device configured to, during a second part of the medical event, monitor the patient and store second clinical information about the patient; a control module configured to receive an indication that the first and second medical devices are to be used on the same patient during the medical event and, based on the indication, establish access by the second medical device to the first clinical information so as to permit the second medical device to conduct, during the medical event, one or more of: (a) displaying at least some of the first clinical information on the second medical device, (b) displaying on the second medical device information derived from at least some of the first clinical information, (c) modifying operation of the second medical device based on the first clinical information, and (d) storing the first clinical information in the second medical device or a remote database.

Example 25. The system of any of Examples 1 to 24, wherein the first medical device is configured to store the first clinical information in a first memory, and the second medical device is configured to store the second clinical information in a second memory, and wherein the control module is further configured to, based on the indication, establish access by the second medical device to the first memory.

Example 26. The system of any of Examples 1 to 25, wherein the first memory and the second memory are part of a same memory device.

Example 27. The system of any of Examples 1 to 26, wherein the second part of the medical event occurs after the first part of the medical event.

Example 28. The system of any of Examples 1 to 27, wherein the control module is further configured establish access by the second medical device in response to determining the first medical device and the second medical device are proximately located.

Example 29. The system of any of Examples 1 to 28, wherein the control module is further configured to prompt for confirmation on either or both of first and second medical, and wherein the prompt includes at least one of a key-code, a visual beacon, a visual light, an audible prompt, and a patient specific input.

Example 30. The system of any of Examples 1 to 29, wherein the control module is further configured to determine the first medical device and the second medical device are proximately located in response to exchange of radio frequency signals.

Example 31. The system of any of Examples 1 to 30, wherein the control module is further configured to determine the first medical device and the second medical device are proximately located in response a receipt of a global positioning system (GPS) signal from each of the first medical device and the second medical device.

Example 32. The system of any of Examples 1 to 31, wherein the control module is further configured to determine the first medical device and the second medical device are proximately located in response to each of the first medical device and the second medical device being connected to a shared local area network (LAN).

Example 33. The system of any of Examples 1 to 32, wherein the control module is further configured to establish access by the second medical device to the first clinical information in response to determining a correlation between the first clinical information and information about one or a combination of the following: an identity of a patient treated with the second medical device, a location of the patient or the second medical device, a time, an identity of a caregiver, and second clinical information gathered by the second medical device.

Example 34. The system of any of Examples 1 to 33, wherein first memory is provided on the first medical device and the second memory is provided on the second medical device.

Example 35. The system of any of Examples 1 to 34, wherein at least one of the first memory and the second memory is located remotely from the first and second medical devices in a network, and wherein the first medical device and the second medical device are wirelessly communicably coupled via the network.

Example 36. The system of any of Examples 1 to 35, wherein the first medical device and the second medical device are configured to directly transfer clinical information the control module is further configured to, based on the indication, establish direct device-to-device access by the second medical device to the first medical device so as to permit the second medical device to access the first clinical information.

Example 37. The system of any of Examples 1 to 36, wherein the medical event is an emergency medical event.

Example 38. The system of any of Examples 1 to 37, wherein the first clinical information details administration of cardiopulmonary resuscitation (CPR) to a patient during the first part of the medical event.

Example 39. The system of any of Examples 1 to 38, wherein the information derived from at least some of the first clinical information includes an indication of CPR quality.

Example 40. The system of any of Examples 1 to 39, wherein the indication of CPR quality includes an indication of chest compression metrics.

Example 41. The system of any of Examples 1 to 40, wherein the information derived from at least some of the first clinical information includes an indication of CPR time.

Example 42. The system of any of Examples 1 to 41, wherein the indication of CPR time includes one or more of: beginning time of CPR administration, ending time of CPR administration, duration of CPR administration, and chest compression timing.

Example 43. A system for hand off of clinical data (e.g. in a medical event) according to an embodiment of the present disclosure includes a patient monitor defibrillator, wherein the patient monitor defibrillator is an advanced life support device, the patient monitor defibrillator comprising a communications module configured to, during a medical event, receive clinical data recorded by one or more of an automated external defibrillator, a ventilation assistance device, and an automated compression device, during the medical event and to conduct, during the medical event, one or more of: (a) displaying at least some of the clinical data on the patient monitor defibrillator, (b) displaying on the patient monitor defibrillator information derived from at least some of the clinical data, (c) modifying operation of the patient monitor defibrillator based on the clinical data, and (d) storing the clinical data in the patient monitor defibrillator.

Example 44. The system of any of Examples 1 to 43, wherein the patient monitor defibrillator and the automated external defibrillator are configured to pair via confirmation on one or both of the patient monitor defibrillator and the automated external defibrillator.

Example 45. The system of any of Examples 1 to 44, wherein the patient monitor defibrillator and the automated external defibrillator are configured to automatically pair in response to determining the patient monitor defibrillator and the automated external defibrillator are proximately located.

Example 46. The system of any of Examples 1 to 45, wherein the patient monitor defibrillator and the automated external defibrillator are configured to determine that the patient monitor defibrillator and the automated external defibrillator are proximately located in response to exchange of radio frequency signals.

Example 47. The system of any of Examples 1 to 46, wherein the patient monitor defibrillator and the automated external defibrillator are configured to determine that the patient monitor defibrillator and the automated external defibrillator are proximately located in response to receipt of a global positioning system (GPS) signal from each of the patient monitor defibrillator and the automated external defibrillator.

Example 48. The system of any of Examples 1 to 47, wherein the patient monitor defibrillator and the automated external defibrillator are configured to determine that the patient monitor defibrillator and the automated external defibrillator are proximately located in response to each of the patient monitor defibrillator and the automated external defibrillator being connected to a shared local area network (LAN).

Example 49. The system of any of Examples 1 to 48, wherein the patient monitor defibrillator and the automated external defibrillator are wirelessly communicably coupled via a network.

Example 50. The system of any of Examples 1 to 49, wherein the patient monitor defibrillator and the automated external defibrillator are wirelessly communicably coupled to provide device-to-device direct transfer of the clinical information between the patient monitor defibrillator and the automated external defibrillator.

Example 51. The system of any of Examples 1 to 50, wherein the medical event is an emergency medical event.

Example 52. The system of any of Examples 1 to 51, wherein the clinical data details administration of cardiopulmonary resuscitation (CPR) to a patient during the medical event.

Example 53. The system of any of Examples 1 to 52, wherein the information derived from at least some of the first clinical information includes an indication of CPR quality.

Example 54. The system of any of Examples 1 to 53, wherein the clinical data is first clinical data, wherein the communications module is further configured to receive the first clinical data in response to determining a correlation between the first clinical data and information about one or a combination of the following: an identity of a patient treated with the patient monitor defibrillator, a location of the patient or the patient monitor defibrillator, a time, an identity of a caregiver, and second clinical data gathered by the patient monitor defibrillator.

Example 55. A method for hand off of clinical data (e.g. in a medical event) according to an embodiment of the present disclosure includes receiving clinical information from a first medical device, the clinical information generated by the first medical device monitoring a patient during a medical event; confirming that a second medical device is to be used on the patient during the medical event; and based on the confirmation, conducting, during the medical event, one or more of: (a) displaying at least some of the clinical information on the second medical device, (b) displaying on the second medical device information derived from at least some of the clinical information, (c) modifying operation of the second medical device based on the clinical information, and (d) storing the clinical information in the second medical device or a remote database.

Example 56. The method of Example 55, wherein the clinical information is generated during a first part of the medical event prior to the patient entering cardiac arrest, wherein the second medical device is used to monitor the patient during a subsequent part of the medical event, and wherein displaying on the second medical device information derived from at least some of the clinical information comprises displaying, on the second medical device, one or more of: (A) displaying a representation of a heart rhythm presenting at a time when the first medical device began monitoring the patient, (B) displaying a representation of a heart rhythm presenting at a time immediately prior to the patient going into cardiac arrest, and (C) displaying a representation of a heart rhythm of the patient at a time subsequent to administration of a shock to the patient's heart.

Example 57. The method of any of Examples 55 to 56, wherein confirming that a second medical device is to be used on the patient during the medical event further comprises providing an indication on at least one of the first medical device and the second medical device that the first medical device and the second medical device are proximately located.

Example 58. The method of any of Examples 55 to 57, wherein the step of confirming further comprises determining that the first medical device and the second medical device are proximately located in response to exchange of radio frequency signals.

Example 59. The method of any of Examples 55 to 58, wherein the clinical information details administration of cardiopulmonary resuscitation (CPR) to a patient during the medical event.

Example 60. The method of any of Examples 55 to 59, wherein the information derived from at least some of the first clinical information includes an indication of CPR quality.

Example 61. The method of any of Examples 55 to 60, wherein the indication of CPR quality includes an indication of chest compression metrics.

Example 62. The method of any of Examples 55 to 61, wherein the information derived from at least some of the first clinical information includes an indication of CPR time.

Example 63. The method of any of Examples 55 to 62, wherein the indication of CPR time includes one or more of: beginning time of CPR administration, ending time of CPR administration, duration of CPR administration, and chest compression timing.

Example 64. The method of any of Examples 55 to 63, wherein the clinical information is first clinical information, and wherein confirming that the second medical device is to be used on the patient during the medical event comprises determining a correlation between the first clinical information and information about one or a combination of the following: an identity of the patient treated with the second medical device, a location of the patient or the second medical device, a time, an identity of a caregiver, and second clinical information gathered by the second medical device.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

Figure 1:
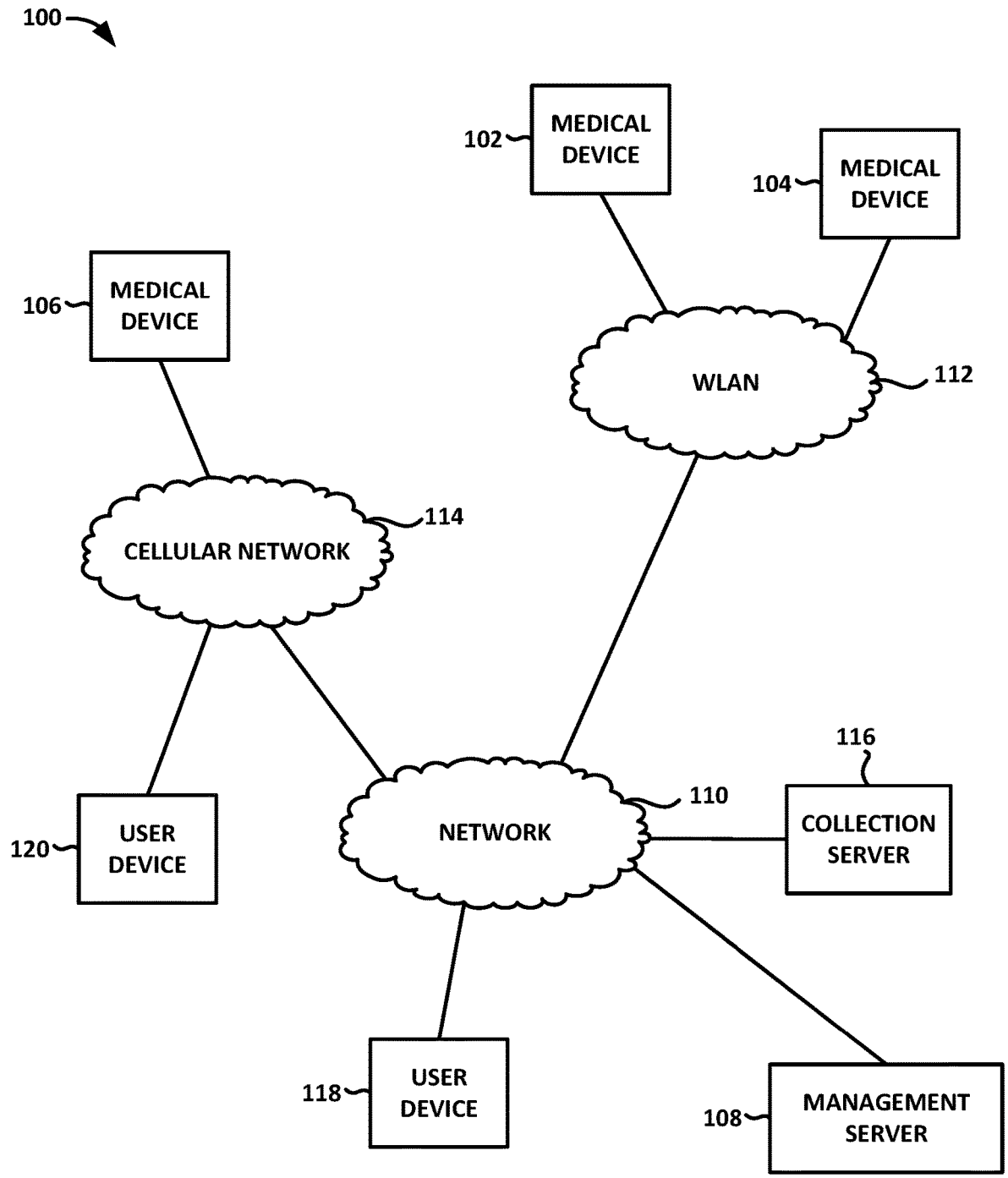
FIG. 1 depicts an illustrative operating environment in accordance with embodiments of the present disclosure.

While the present invention is amenable to various modifications and alternative forms, specific embodiments have been shown by way of example in the drawings and are described in detail below. The present invention, however, is not limited to the particular embodiments described. On the contrary, the present invention is intended to cover all modifications, equivalents, and alternatives falling within the ambit of the present invention as defined by the appended claims.

Although the term "block" may be used herein to connote different elements illustratively employed, the term should not be interpreted as implying any requirement of, or particular order among or between, various steps disclosed herein unless and except when explicitly referring to the order of individual steps.

DETAILED DESCRIPTION

Various types of facilities (for example, hospitals, schools, office buildings, airplanes, busses, etc.) may be equipped with one or more medical devices configured for different types of use in medical situations. As used herein, the phrases "medical situations" and "medical events" are used in their broadest sense to refer to any situation or event in which medical attention is called for, in which a patient experiences a medical problem, or in which a patient has treatment or care. For example, and without limitation, a medical event may begin when a patient experiences medical symptoms or an incident and/or a call is made to emergency services (e.g. emergency medical services), and the medical event may end when the patient has been evaluated, treated, transported, and/or released. A medical event or situation may include various events within the medical event, including for example emergency transport.

In addition, more than one type of medical device may be used in the medical/emergent situations. For example, automated external defibrillators (AEDs) are designed to be used in medical situations involving a victim of cardiac arrest, and may be used by a first responder prior to a trained emergency medical technician responding to assist with the victim of cardiac arrest. The emergency medical technician may use a different or additional medical device to treat the victim. Moreover, one or more medical devices may be used in an ambulance or prior a victim's arrival at a hospital. Once the victim arrives at the hospital, different and additional medical devices may be used by other types of medical personnel such as emergency medical physicians and nurses.

According to embodiments, medical devices are configured to communicate between the devices so as to permit clinical information captured on one of the medical devices to be displayed and/or stored on the other of the medical devices and/or a remote database and/or associated with the corresponding patient's records or files, and/or permit one of the medical devices to modify the operation of the other of the medical devices based on collected clinical information. A treating clinician will have the ability to view the "complete" event detail and see the complete event, e.g., from when an AED was turned on to when a patient arrives at a treatment facility. Access is controlled between the medical devices in order to ensure the correct clinical information is communicated, and to ensure that a given medical device is authenticated, capable of and allowed to access clinical information captured on another medical device.

FIG. 1 depicts an illustrative operating environment 100 (and, in some embodiments, aspects of the present invention) in accordance with embodiments of the present disclosure, as illustrated by way of example. As shown in FIG. 1, the illustrative operating environment 100 includes a number of medical devices 102, 104, and 106 that communicate with one or more management servers 108 via one or more networks 110. The network 110 may be, or include, any number of different types of communication networks such as, for example, a short messaging service (SMS), a local area network (LAN), a wireless LAN (WLAN), a wide area network (WAN), the Internet, a peer-to-peer (P2P) network, a direct wired connection between two or more devices (for example, an RS-232 connection), a direct wireless connection between two or more devices (for example, a Bluetooth® connection), and/or the like. In embodiments, the network 110 may be a combination of networks.

The medical devices 102, 104, and/or 106 may be configured for infrequent use in emergent or medical situations. For example, the medical devices 102, 104, and 106 may include, for example, an automated external defibrillator (AED), a portable infuser, and/or the like. The medical devices 102, 104, and/or 106 may be, for example, defibrillators (for example, ZOLL® X-Series®, E-Series®, or R-Series® devices), automatic external defibrillators (AEDs) (for example, ZOLL® AED Pro® devices, ZOLL® AED Plus® devices), wearable cardioverter defibrillators (for example, ZOLL® LifeVest® devices), portable electronic infusion pumps (for example, ZOLL® Power Infuser® devices), device systems (for example, ZOLL® Propaq® systems), compression assistance devices or technologies (for example, ZOLL® Real CPR Help®, ZOLL® AutoPulse®, or ZOLL® PocketCPR®), ventilation assistance devices (for example, IMPACT® Instrumentation ventilators) and/or the like. The medical devices 102, 104, and/or 106 may be configured to provide therapy (for example, defibrillation shocks, infused medicines, and/or the like), and/or to monitor, detect, and/or derive or calculate various physiological parameters such as, for example, heart rate, blood pressure, temperature, respiration rate, blood oxygen level, end-tidal carbon dioxide level, pulmonary function, blood glucose level, weight, and/or the like. In embodiments, the medical devices 102, 104, and/or 106 may determine and/or present waveforms such as, for example, electrocardiographs (ECGs).

In certain instances, one or more of the medical devices 102, 104, and 106 is used during a first part of an emergency medical event, and/or one or more of the other medical devices 102, 104, and 106 is used during a second part of the emergency medical event. For example, the medical devices 102, 104, and/or 106 used during the first part of an emergency medical event may include an automated external defibrillator (AED), a portable infuser, and/or the like, as would be operated by a first responder to an emergency medical event. Other types of medical devices 102, 104, and/or 106 can also be used such as, for example, during a second part of an emergency medical event including defibrillators (for example, ZOLL® XSeries® or ESeries® devices), ventilation assistance devices, and/or compression assistance devices, as would be carried by an EMT responding to the emergency medical event.

In embodiments, the medical devices 102, 104, and/or 106 are disposed at the same location or different locations. For example, an organization may install one or more medical devices 102, 104, and/or 106 at various facilities, in various geographic locations, and/or the like. In embodiments, the medical devices 102, 104, and/or 106 may be managed by a single entity or different entities. As shown, different medical devices 102, 104, and 106 may be configured to communicate with other devices using different types of networks, combinations of networks, and/or the like. For example, medical devices 102 and 104 may be configured to communicate via a wireless local access network (WLAN) 112, while medical device 106 may be configured to communicate via a cellular network 114. In embodiments, the medical devices 102, 104, and/or 106 may include technology that enables communication through different types of networks, thereby enabling a medical device 102, 104, and/or 106 to transition from one type of network to another.

According to embodiments, the medical devices 102, 104, and/or 106 are configured to provide information, such as, device-readiness information, device performance information, clinical event information, and/or the like, to the management server 108. Device-readiness information or data may include any information associated with the condition of one or more components of the medical device that may have bearing on the ability of the medical device to perform a function for which it was designed. For example, device-readiness information may include information associated with a condition, status, and/or remaining life of a battery or batteries, an electrode, a sensor, a communication component, and/or the like. Device performance information or data may include any information associated with a performance of a component and/or function of the medical device. For example, device performance information may include information about functions a medical device performed during a medical and/or emergent situation such as, for example, a manner in which a defibrillation shock was applied during a cardiac arrest situation, an energy level of an applied shock during the situation, a number of times a shock was applied during the situation, and/or the like. Clinical event information or data may include any information, recorded during a clinical event, associated with a patient. For example, clinical event information may include physiological parameters, patient demographic information, patient ECG data, device prompting records, device actions and operations, CPR performance data, faults, errors, and/or voice recording, and/or the like.

The medical devices 102, 104, and/or 106 are communicably coupled to the management server 108, and, in some embodiments, are configured to communicate directly with the management server 108, while, in other embodiments, the medical devices 102, 104, and/or 106 are configured to communicate with a collection server 116, which is configured to communicate with the management server 108. In embodiments, to improve efficiencies all of the medical devices 102, 104, and/or 106 may be configured to provide information to the management server 108 by transmitting the information to a single uniform resource locator (URL). Although the management server 108 and the collection server 116 are each referred to herein in the singular, the management server 108 and the collection server 116 may be implemented in multiple server instances (for example, as a server cluster), distributed across multiple computing devices, instantiated within multiple virtual machines, and/or the like.

Additionally, there may be user devices such as an Apple iPad, iPhone or iWatch or bodily-attached devices such as Google Glass that may be used by medical personnel for either viewing particular data from one or both the local medical devices 102, 104 and the remote medical devices 106. In this description, these user devices that display or otherwise communicate with medical personnel ef-particular data from medical devices 102, 104 are also termed within this application as medical devices, for example. In other embodiments, one of the medical devices within the area of the WLAN (e.g. 110) may provide the server functionality and be the server device to provide the network at the local level 112, in addition to being the medical device 102, 104. One of the local medical devices 102, 104 may also provide router functionality to route the communication traffic between the medical devices 102, 104 at the local area.

A secure, dynamically reconfigurable network may be provided for the medical devices 102, 104 in the vicinity of each other as new medical devices arrive on scene (e.g. at a location of a medical event), and leave as medical personal depart, in a dynamic fashion. In some embodiments the network is self-configurable; that is, the medical devices and the other user devices themselves provide any necessary server, routing and other communication functions. This configuration may be implemented in a mobile environment, for example in a pre-hospital environment, treating a patient for a medical condition at the patient's home or in a public space. In a hospital environment, wireless routers are ubiquitous, thereby providing access to a more capable server residing separately from the local medical devices on the hospital network. When the medical device provides the server function, the data collected from itself and the other local devices may be stored temporarily on the server medical device until it is able to communicably connect in a secure fashion to the main collection server 116 and/or management server 108.

In one embodiment, the local network between the medical devices is dynamically and securely established by first employing network cloaking by the server, according to which, for example, the server suppresses the broadcasting of its Service Set Identifier (SSID). Any additional medical or user devices can then only join when they explicitly request that SSID, according to one embodiment. That unbroadcast, preknown SSID may be as simple as "ZOLL-MEDICAL" or may be a more complex, apparently random sequence of alphanumerics that may be generated via an encryption algorithm, using a master key known only to devices that are proprietary to a common originator (e.g. devices originating with ZOLL Medical Corporation) or known only to devices which have been provided with the same master key. In some cases, such master keys may be further encrypted at the time of the event using a seed that incorporates, for instance, the date.

As described by Wikipedia and other sources, in some embodiments, there may be only pre-approved MAC addresses and MAC filtering employed. Pre-shared key mode (PSK, also known as Personal mode) may also be employed. Both WPA2-PSK and WPA2-EAP result in a Pairwise Master Key (PMK) known to both the supplicant (client) and the authenticator (AP). (In PSK the PMK is derived directly from the password, whereas in EAP it is a result of the authentication process.) The four-way WPA2 handshake essentially makes the supplicant and authenticator prove to each other that they both know the PMK, and creates the temporal keys used to actually secure network data.

Capturing the four-way handshake does not divulge the PMK or PSK (since capturing the handshake is easily achieved over wireless). The PMK is also not sent during the handshake, but is instead used to calculate a Message Integrity Check (MIC). A 256 bit Master key (PMK) may be generated using a combination of passphrase and the SSID. However this PMK is not exchanged during the handshake, according to one embodiment. What is exchanged according to such embodiment are Nonce values (random numbers). AP sends A-Nonce in message 1. Station sends S-Nonce in message 2. The session key may be generated using a combination of things: the 2 Nonces and the PMK and Mac address, according to one embodiment.

Figure 8:
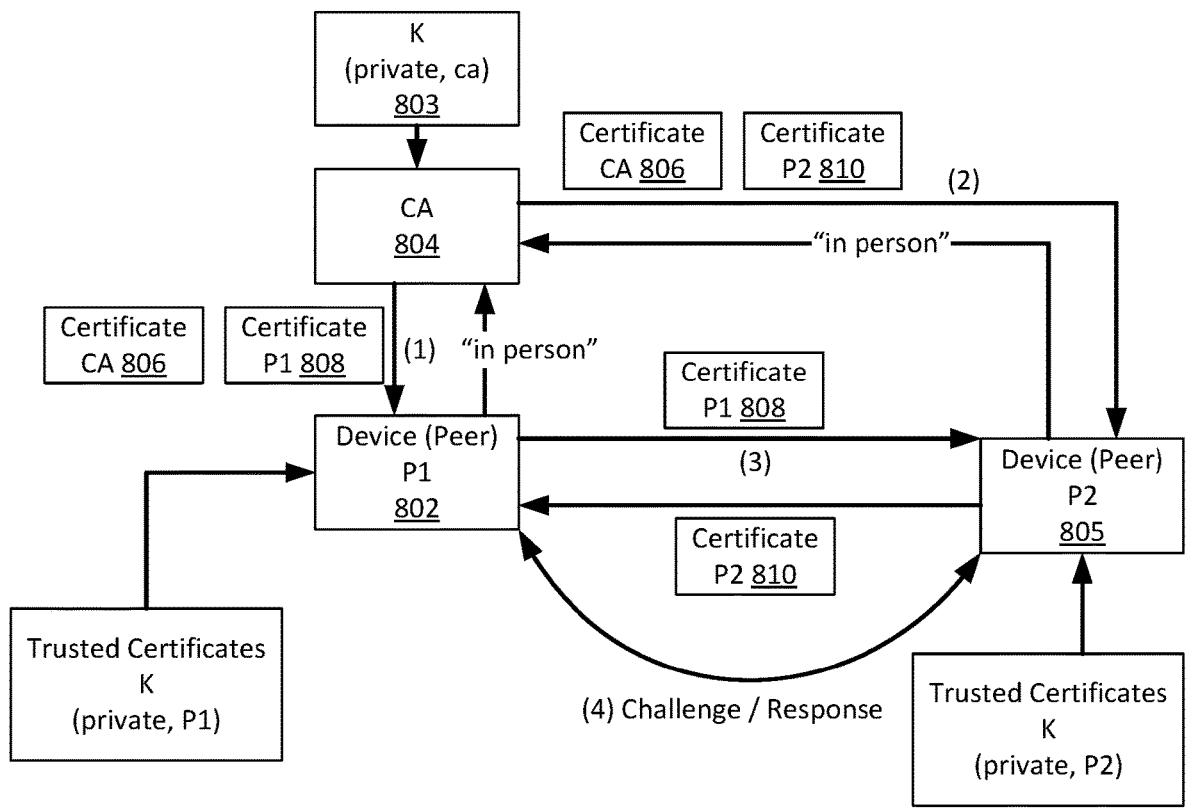
FIG. 8 illustrates an example of public key infrastructure.

Alternatively, a public key infrastructure (PKI) may be used for establishing a secure channel. In a public-key infrastructure (PKI), certificates are used for the purpose of authentication. A certificate is a virtual document that allows an authenticator to verify the identity of a user without having any prior knowledge about the user (such as a pre-shared key used in PSK), according to one example. Several forms of public-key infrastructures exist. FIG. 8 is one example of a PKI authentication architecture. In the figure, the numbers indicate the order of events. In FIG. 8, a PKI architecture is shown in simple form, in which one extra entity is involved called the certificate authority (CA) 804. The set up process for all peers is to get a certificate at the CA 804. The CA is responsible for checking the identity one time "in person." In the case of a near-field communication (NFC) mobile phone for example, the set up process could be done during the manufacturing of the phone and/or secure element as the "in person" checkin. After the CA 804 has verified the identity of a requester, called peer 1 (P1) 802, it creates and signs a certificate Cp1 808. A well known standard for certificates is X.509 defined in RFC 2459. The information 1 on the certificate 808 includes the identity information of the peer (which may be referred to as Ip1) and the CA that signed it (which may be referred to as Ica), a public key (Kpub, p1) and a signature (Sp1).

The signature is calculated by hashing and encrypting Kpub, p1 and Ip1 using the CA's private key (Kpriv, ca) 803. After signing, the CA 804 gives the requester 802 its certificate $C_{p1}$ 808. Furthermore, the CA 804 provides its own certificate (Cca) 806 to the requester containing the public key (Kpub, ca). Cca 806 is a special type of certificate indicating that it can be used to sign other certificates but $C_{CA}$ is not signed itself, according to one example. After this, the set up process is finished, according to one example.

All peers keep a list of CA certificates that are trusted which, in this example, implies that every peer with a certificate signed by one of the CAs in its list is trusted. Therefore, this list may be chosen carefully and protected from unintended change, in such examples. When two peers, p1 802 and p2 805, want to authenticate each other, they first exchange certificates. They each verify that the certificate was signed by a CA that they trust. This is done by decrypting the signature on the peer peers-certificate with the public key of the CA (which is on the certificate of the CA). Subsequently, the peers each verify that the other owns the private key corresponding to the public key on the certificate. This can be done by a challenge/response mechanism similarly as done in PSK. Private keys remain confidential to their owners, in this example, including the private key of the CA 804. Though in the example discussed here, a PKI with one CA has been described, it is possible to have a hierarchical infrastructure of certificate authorities, in which certificate authorities in tier 2 have a certificate signed by a certificate authority in tier 1, which in turn is signed by the root certificate authority. The root certificate authority may have a self-signed certificate meaning that the signature is calculated from its own private key, in some cases, in which the certificate authorities below the root certificate authority inherit the trustworthiness of the root certificate authority. This architecture may be useful in large systems for load balancing. PKI schemes like EAP-TLS, EAP-TTLS, EAP-IKEv2 may be employed, or other schemes known to those skilled in the art, based on the present disclosure.

Alternatively, the dynamically reconfigurable and secure mesh networking protocol such as ZigBee may be employed. Zigbee is a specification for a suite of high-level communication protocols used to create personal area networks built from small, low-power digital radios, and is based on an IEEE802.15.4 standard.

According to some embodiments, and as described by Wikipedia and other sources, ZigBee devices may be of three types:

First, a ZigBee Coordinator (ZC): The most capable device, the Coordinator forms the root of the network tree and might bridge to other networks, according to some embodiments. There is exactly one ZigBee Coordinator in each network since it is the device that started the network originally (the ZigBee LightLink specification also allows operation without a ZigBee Coordinator, making it more usable for over-the-shelf home products), according to some embodiments. It stores information about the network, including acting as the Trust Center & repository for security keys, according to some embodiments.

Second, a ZigBee Router (ZR): As well as running an application function, a Router can act as an intermediate router, passing on data from other devices, according to some embodiments.

Third, a ZigBee End Device (ZED): Contains just enough functionality to talk to the parent node (either the Coordinator or a Router); it cannot relay data from other devices, according to some embodiments. This relationship allows the node to be asleep a significant amount of the time thereby giving long battery life, according to some embodiments. A ZED requires the least amount of memory, and therefore can be less expensive to manufacture than a ZR or ZC, according to some embodiments.

The current ZigBee protocols support beacon and non-beacon enabled networks. In non-beacon-enabled networks, an unslotted carrier sense multiple access with collision avoidance (CSMA/CA) channel access mechanism is used. In this type of network, ZigBee Routers typically have their receivers continuously active, requiring a more robust power supply, according to some embodiments. However, this allows for heterogeneous networks in which some devices receive continuously, while others only transmit when an external stimulus is detected, according to some embodiments.

In beacon-enabled networks, the special network nodes called ZigBee Routers transmit periodic beacons to confirm their presence to other network nodes, according to some embodiments. Nodes may sleep between beacons, thus lowering their duty cycle and extending their battery life, according to some embodiments. Beacon intervals depend on data rate; they may range from 15.36 milliseconds to 251.65824 seconds at 250 kbit/s, from 24 milliseconds to 393.216 seconds at 40 kbit/s and from 48 milliseconds to 786.432 seconds at 20 kbit/s, according to some embodiments. However, low duty cycle operation with long beacon intervals often benefits from precise timing, which can conflict with a need for low product cost, according to some embodiments.

In general, the ZigBee protocols minimize the time the radio is on, so as to reduce power use, according to some embodiments. In beaconing networks according to some embodiments, nodes only need to be active while a beacon is being transmitted. In non-beacon-enabled networks according to some embodiments, power consumption is asymmetrical: some devices are always active, while others spend most of their time sleeping. ZigBee uses 128-bit keys to implement its security mechanisms, according to some embodiments. A key can be associated either to a network, being usable by both ZigBee layers and the MAC sublayer, or to a link, acquired through pre-installation, agreement or transport, according to some embodiments. Establishment of link keys may be based on a master key which controls link key correspondence, according to some embodiments. Ultimately, at least the initial master key is obtained through a secure medium (transport or pre-installation), as the security of the network may depend on it, according to some embodiments. Link and master keys are only visible to the application layer, according to some embodiments. Different services use different one-way variations of the link key in order to avoid leaks and security risks, according to some embodiments.

As shown in FIG. 1, user devices 118 and 120 may be communicably coupled to the management server 108 and may be configured to access services provided by the management server 108. For example, the management server 108 may facilitate providing information received from the medical devices 102, 104, and/or 106 to the user devices 118 and/or 120. Additionally, users may utilize the management server 108, via the user devices 118 and/or 120, to configure the medical devices 102, 104, and/or 106, to provide software updates to them, and/or the like.

As used herein, the phrase "communicably coupled" is used in its broadest sense to refer to any coupling whereby information may be passed. Thus, for example, communicably coupled includes electrically coupled by, for example, a wire; optically coupled by, for example, an optical cable; and/or wirelessly coupled by, for example, a radio frequency or other transmission media. "Communicably coupled" also includes, for example, indirect coupling, such as through a network or a series of devices and/or communication protocols, or direct coupling.

The illustrative operating environment 100 shown in FIG. 1 is not intended to suggest any limitation as to the scope of use or functionality of embodiments of the present invention. Neither should the illustrative operating environment 100 be interpreted as having any dependency or requirement related to any single component or combination of components illustrated therein. Additionally, any one or more of the components depicted in FIG. 1 or described herein may be, in embodiments, integrated with various ones of the other components depicted therein (and/or components not illustrated), all of which are considered to be within the ambit of the present invention. For example, the collection server 116 may be integrated with the management server 108, and the network 110 may be included by, or be included within, the WLAN 112, and/or the cellular network 114.

According to embodiments, various components of the operating environment 100, illustrated in FIG. 1, can be implemented on one or more computing devices. For example, one or more of the medical devices 102, 104, 106; the management server 108, the collection server 116, and the user devices 118 and 120 may include, be communicatively coupled to, and/or be included within, one or more computing devices. A computing device may include any type of computing device suitable for implementing embodiments of the invention. Examples of computing devices include specialized computing devices or general-purpose computing devices such "workstations," "servers," "laptops," "desktops," "tablet computers," "hand-held devices," components of medical devices, and/or the like, all of which are contemplated within the scope of FIG. 1 and reference to various components of the operating environment 100.

Figure 2:
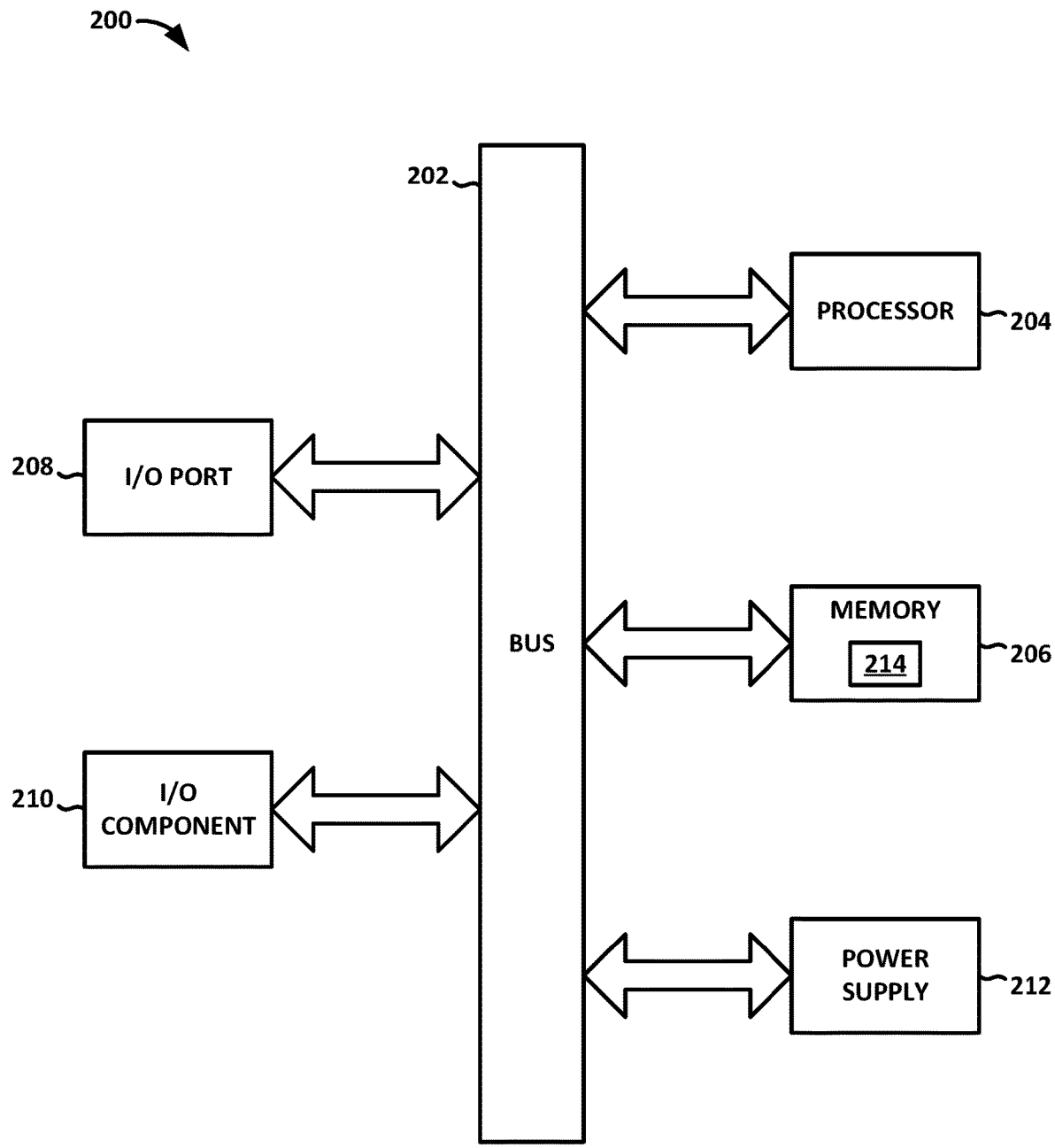
FIG. 2 depicts an illustrative computing device in accordance with embodiments of the present disclosure.

As shown in FIG. 2, a computing device 200 includes a bus 202 that, directly and/or indirectly, couples one or more of the following devices: a processor 204, a memory 206, an input/output (I/O) port 208, an I/O component 210, and a power supply 212. Any number of additional components, different components, and/or combinations of components may also be included in the computing device 200. The bus 202 may represent one or more busses (such as, for example, an address bus, data bus, and/or combination thereof). Similarly, in embodiments, a computing device 200 may include a number of processors 204, a number of memory components 206, a number of I/O ports 208, a number of I/O components 210, and/or a number of power supplies 212. Additionally, any number of these components, and/or combinations thereof, may be distributed and/or duplicated across a number of computing devices 200.

Although the various components of FIG. 2 are shown as distinct components for the sake of clarity, in reality, delineating various components of a computing device 200 may not be as clear. For example, I/O components 210 may include devices contained within the computing device 200 and/or devices that are separate from the computing device 200. As another example, processors 204 may have memory. As such, the diagram of FIG. 2 is merely illustrative of an example of a computing device 200 that may be used in connection with one or more embodiments, but any number of other configurations for a computing device 200 that can execute computer-executable instructions to accomplish various aspects of embodiments described herein are also considered to be within the ambit of the invention.

According to various embodiments, the processor 204 (or processors) reads data from various entities such as the memory 206, I/O components 210, and/or the like. For example, in embodiments, the processor 204 may execute computer-executable instructions 214 that are stored in the memory 206. Additionally, in embodiments, the processor 204 may receive computer-executable instructions, signals, and/or other types of information from one or more I/O components 210. As the processor 204 reads and manipulates information, it may also cause information to be stored in the memory 206.

In embodiments of the present disclosure, the memory 206 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; or any other medium that can be used to encode information and can be accessed by a computing device such as, for example, quantum state memory, and/or the like.

Figure 3:
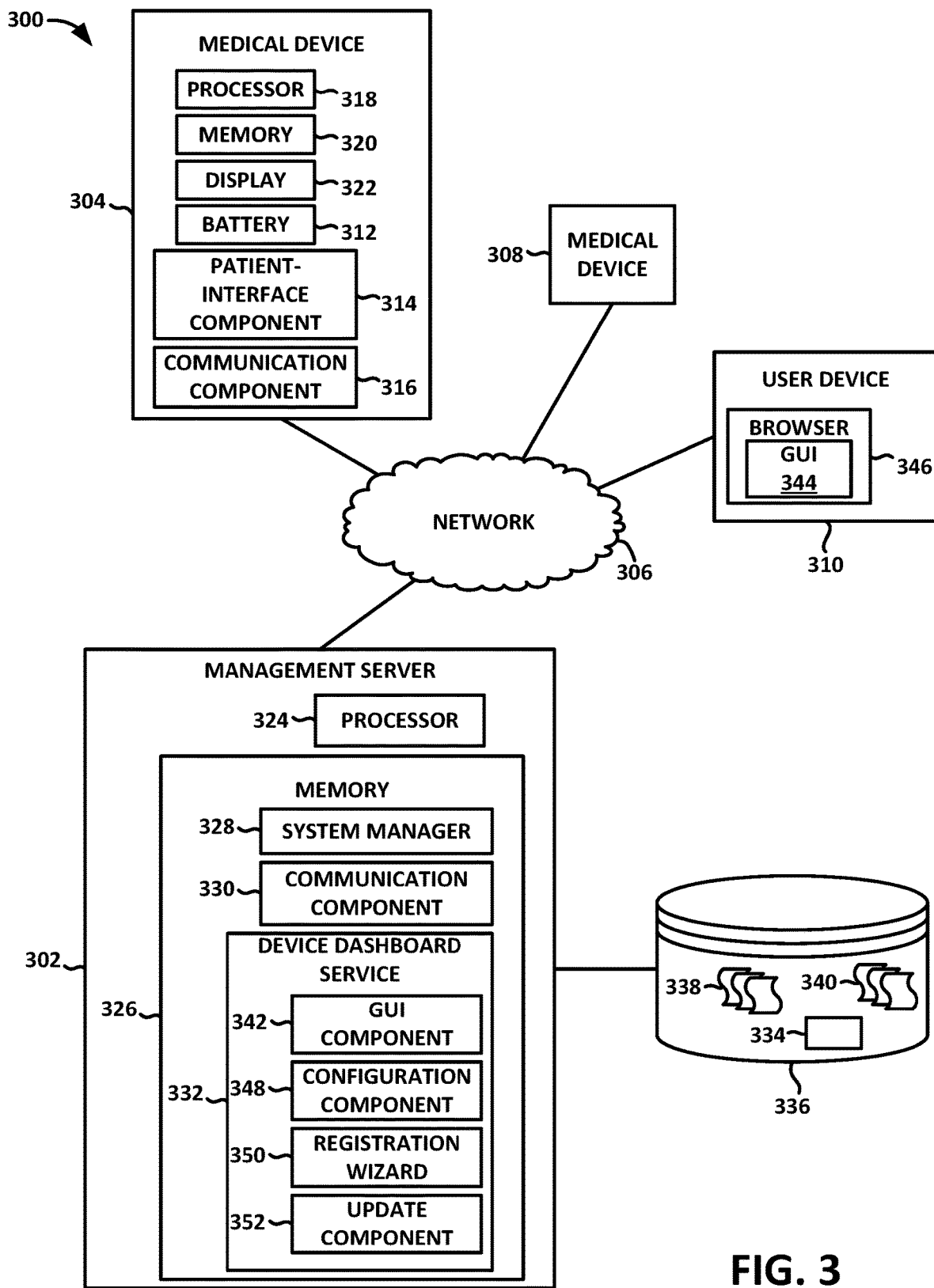
FIG. 3 depicts another illustrative operating environment in accordance with embodiments of the present disclosure.

In embodiments, the memory 206 stores computer-executable instructions for causing the processor 204 to implement aspects of embodiments of system components discussed herein and/or to perform aspects of embodiments of methods and/or procedures discussed herein. Computer-executable instructions may include, for example, computer code, machine-useable instructions, and the like such as, for example, program components capable of being executed by one or more processors associated with a computing device. Examples of such program components are depicted in FIG. 3, and may include the system manager 328, the communication component 330, the device dashboard 332 (and components thereof), the database 336, and/or the like. Some or all of the functionality contemplated herein may also, or alternatively, be implemented in hardware and/or firmware.

In embodiments of the present disclosure, upon being executed by one or more processors, computer-executable instructions may cause the one or more processors to initiate one or more components, e.g. a communication component. The components may be, or include, program components, electrical circuits, logic modules, mechanical assemblies, and/or any number of different types of combinations of hardware, firmware, and software. As the term is used herein, "initiate" may include instantiate, create, activate, utilize, and/or the like. That is, for example, the components initiated by a processor may be software components created, instantiated, or otherwise invoked by the processor. As another example, the components may include hardware (for example, electronic circuits) activated by the processor. As such, a "component" which may also be referred to as a "module" or a "control module" or "communications module" may be initiated and/or implemented in, or as a combination of two or more of, hardware, software, and firmware, and may be initiated and/or instantiated and/or located in one device or place, or alternatively distributed across multiple devices and/or places and/or in the network 110 or the cloud.

In embodiments, the I/O port 208 may allow the computing device 200 to be logically coupled to other devices including external devices and/or I/O components 210, some of which may be built in. Examples of I/O components 210 include a microphone, joystick, game pad, satellite dish, scanner, printer, wireless device, keyboard, pen, voice-input device, touch-input device, touch-screen device, interactive display device, a mouse, and the like. In embodiments, the I/O component 210 may include, for example, a presentation component (for example, a display, a printing device, a touch-screen I/O display, etc.), a communication component (for example, a transceiver, an antenna, etc.), and/or the like.

The illustrative computing device 200 shown in FIG. 2 is not intended to suggest any limitation as to the scope of use or functionality of embodiments of the present invention. Neither should the illustrative computing device 200 be interpreted as having any dependency or requirement related to any single component or combination of components illustrated therein. Additionally, any one or more of the components depicted in FIG. 2 may be, in embodiments, integrated with various ones of the other components depicted therein (and/or components not illustrated), all of which are considered to be within the ambit of the present invention.

FIG. 3 depicts an illustrative operating environment 300 in accordance with embodiments of the invention. The illustrative operating environment 300 includes a management server 302 that is configured to communicate with a medical device 304 via a network 306. Any number of additional medical devices 308 may be configured to communicate with the management server 302, as well. The communication between the management server 302 and the medical device 304 and/or 308 may be unidirectional or bidirectional. According to embodiments, a user may utilize a user device 310 to communicate with the management server 302. The management server 302 may be (or be similar to), for example, the management server 108 depicted in FIG. 1; the medical device 304 and/or 308 may be (or be similar to), for example, the medical devices 102, 104 and/or 106 depicted in FIG. 1; the network 306 may be (or be similar to) any one or more of the networks 110, 112, and 114 depicted in FIG. 1; and the user device 310 may be (or be similar to) the user devices 118 and/or 120 depicted in FIG. 1.

The medical device 304 may be powered by one or more batteries 312 and may include a patient-interface component 314 configured to provide treatment to, and/or obtain physiological parameter measurements from, a patient; and a communication component 316 configured to facilitate transmitting information through the network 306 to the management server 302. In embodiments, the patient-interface component 314 may be, or include, one or more defibrillation electrodes (pads), one or more infusion needles, and/or the like. The medical device 304 also may include a processor 318 and a memory 320.

The medical device 304 may receive signals from one or more patient-interface components 314 (for example, sensors or electrodes) coupled to a patient and use the processor 318 to analyze the signals to monitor, detect, and/or derive or calculate various physiological parameters. For example, the processor 318 may monitor, detect, and/or derive or calculate heart rate, blood pressure, temperature, respiration rate, blood oxygen level, end-tidal carbon dioxide level, pulmonary function, blood glucose level, weight, and/or the like. Any one or more of these physiological parameters, other measured parameters, other derived parameters, and/or the like may be stored in the memory 320. In some embodiments, the medical device 304 includes a display 322 for presenting data associated with one or more of the above physiological parameters, other clinical event information, configuration options, and/or the like. Clinical event information (for example, physiological parameters, device usage metrics, and/or the like, recorded during use of the medical device 304 during a clinical event), self-test information, configuration information, and/or the like may be stored in the memory 320.

The communication component 316 may include I/O ports (for example, logical ports, virtual ports, physical ports, etc.), one or more antenna, one or more transceivers, one or more receivers, and/or the like. In embodiments, for example, the communication component 316 may include I/O ports such as, for example, an RS-232 port for use with a modem based dialup connection, a copper or fiber 10/100/1000 Ethernet port, a Bluetooth® or WiFi interface, an infrared port, a universal serial bus (USB) port, and/or the like. In embodiments, the communication component 316 may be configured to facilitate near-field communications, cellular communications, and/or the like.

In embodiments, the medical device 304 may be configured to transmit information to the management server 302, receive communications from the management server 302, and/or facilitate management of patient data, device status and history, device error logs, and/or the like. The medical device 304 may be configured to receive software updates and configuration information via the communication component 316. In embodiments, the medical device 304 may be configured to transmit self-test information, clinical event information, alarm information, to the management server 302 automatically (for example, according to a programmed schedule, in response to an event, and/or the like) and/or manually (for example, in response to a user input).

As shown in FIG. 3, the management server 302 may be implemented on a computing device that includes a processor 324 and a memory 326. In embodiments, the management server 302 may refer to hardware, software, firmware, or a combination of these, and may be, or include, a computing device, a number of computing devices, a virtual machine, a number of virtual machines, a service, and/or the like. For example, the management server 302 may be a stand-alone server device or server bank. In embodiments, the management server 302 may be software configured to be executed by a computing device such as, for example, the user device 310. Various program components such as, for example, a system manager 328, a communication component 330, and/or device dashboard service 332 may be stored in the memory 326. In embodiments, the processor 324 executes the system manager 328, the communication component 330, and/or the device dashboard service 332.

The system manager 328 may facilitate management of various aspects of the medical devices 304 and/or 308, the device dashboard service 332, and/or the like. For example, the system manager 328 may be configured to coordinate communications between the management server 302 and the medical devices 304 and/or 308; facilitate login and authentication procedures; create, delete, manipulate, and manage user accounts and account information 334 stored in a database 336; interact with, query, and/or index the database 336; facilitate integration with other systems (for example, electronic medical record (EMR) systems, administration systems, and/or insurance/billing systems); facilitate operations and procedures for maintaining compliance with relevant laws and regulations; facilitate configuration and/or customization of various aspects of embodiments of the management server 302; and/or the like. The database 336 may be, or include, one or more tables, one or more relational databases, one or more multi-dimensional data cubes, one or more non-relational databases, and/or the like. Further, though illustrated as a single component, the database 336 may, in fact, be a plurality of databases 336 such as, for instance, a database cluster, which may be implemented on a single computing device or distributed among a number of computing devices, memory components, and/or the like.

The communication component 330 may include similar aspects as the communication component 316 of the medical device 304, and may be configured to communicate with the communication component 316 of the medical device 304. This communication between communication component 330 and communication component 316 may be direct device-to-device communication, and/or indirect communication via network 306 and/or via one or more other devices 308, 310, 336. In embodiments, the operating environment 300 may include a collection server (such as, for example, the collection server 116 depicted in FIG. 1), in which case the communication component 330 may be configured to communicate with a communication component of the collection server, which may be configured to communicate with the communication component 316 of the medical device 304. In embodiments, the communication component 330 may also be configured to facilitate communications between the management server 302 and the medical device 308, the user device 310, other devices, other systems, and/or the like.

In embodiments, the communication component 330 may be configured to receive device-readiness information 338 and/or clinical event information 340 from the medical devices 304 and/or 308, for example wirelessly. The received information 338 and/or 340 may be stored in the database 336, as shown. According to embodiments, the communication component may also be configured to receive information (for example, device-readiness information and/or clinical event information) from a USB flash drive, a CD-ROM disc, and/or any number of other storage and/or transmission media.

Figure 5:
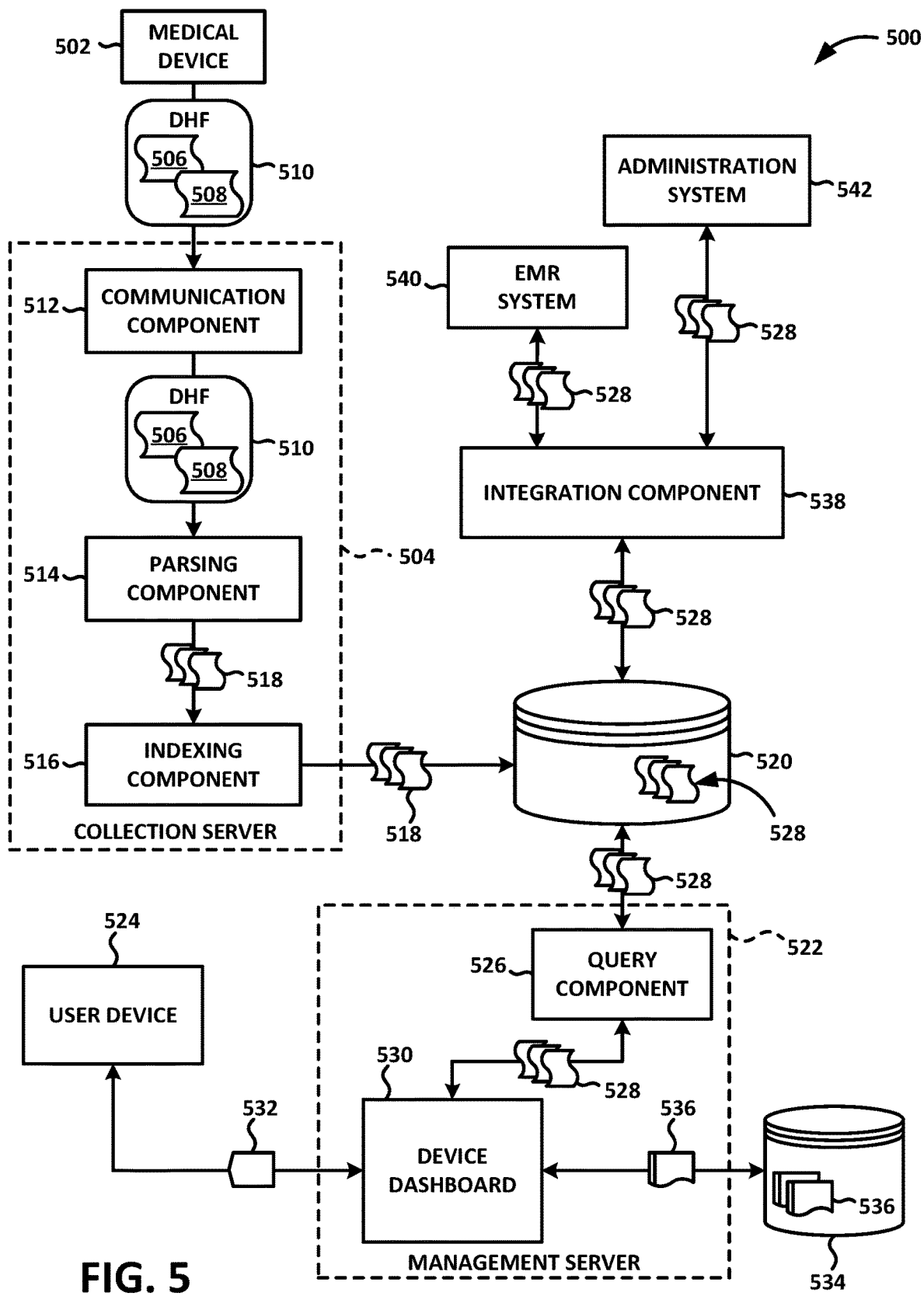
FIG. 5 depicts an illustrative operation of an operating environment in accordance with embodiments of the present disclosure.
Figure 6:
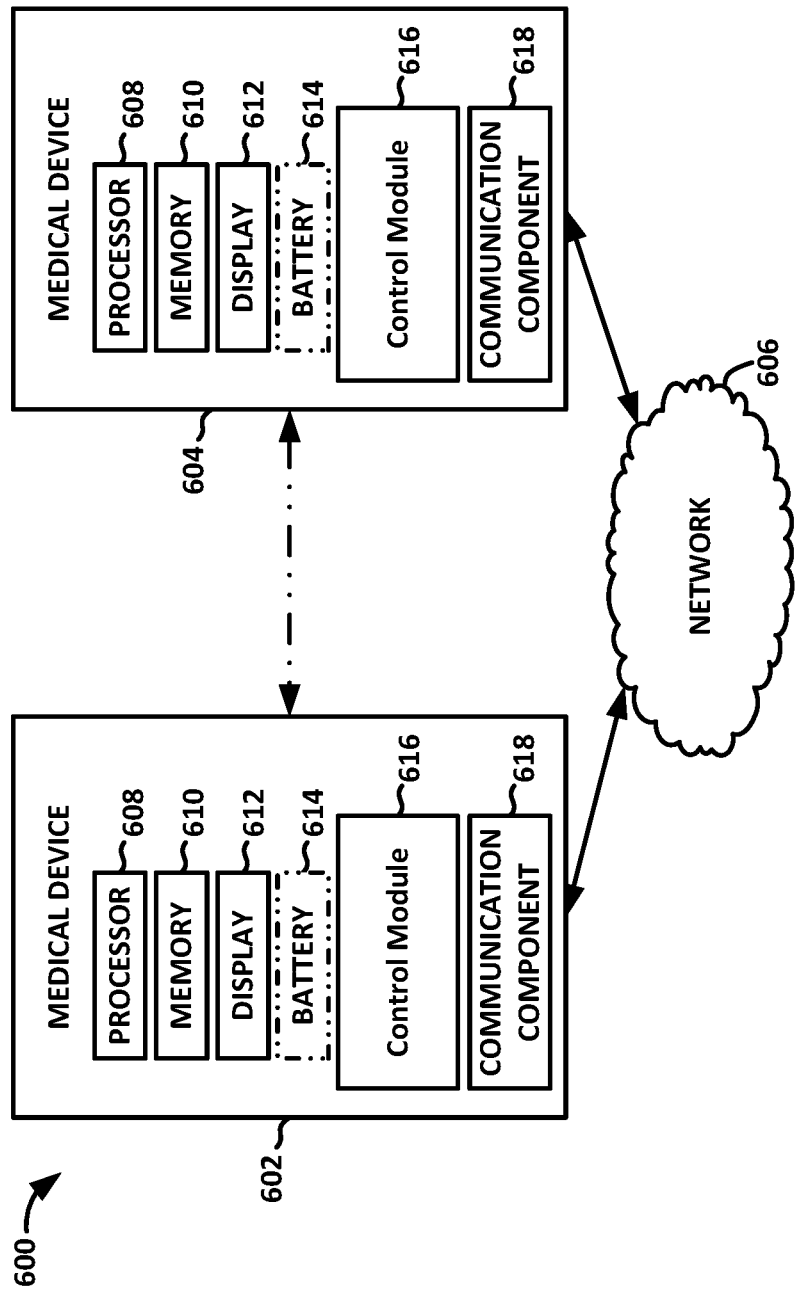
FIG. 6 depicts an illustrative data sharing system including one or more medical devices in accordance with embodiments of the present disclosure.

Although communication components 316 and 330 (and 512 and 618) are shown as boxes associated with devices in FIGS. 3, 5, and 6, as described above such "components" or "modules" or "control modules" may be initiated and/or implemented in, or as a combination of two or more of, hardware, software, and firmware, and may be initiated and/or instantiated and/or located in one device or place, or alternatively distributed across multiple devices and/or places. For example, any one of communication components 316, 330, 512, and/or 618 may be hardware, software, firmware, or some combination thereof, and may be initiated in or on the same device that is collecting information or data being communicated, distributed across multiple devices, and/or on a device different from the device that is collecting the information or data being communicated.

According to embodiments, the device dashboard service 332 may be an application configured to assist users with the management of their medical devices. The device dashboard service 332 may serve as a central location for a user to manage their medical devices. Access to the device dashboard service 332 may be web based with the option for customers to add the application to their computer system/network. The device dashboard service 332 may be configured to be compatible with any number of different medical devices and may be configured to allow the user to input additional information about their medical devices, competitor devices, and/or the like. In this manner, the device dashboard service 332 may, in embodiments, facilitate organizing and simplifying medical device management, remotely monitoring medical devices; remotely managing AED software; remotely configuring medical devices; viewing clinical event information; viewing device-readiness (self-test) information; and/or the like.

According to embodiments, the device dashboard service 332 may be configured to facilitate management of the medical devices 304 and 308-306, information received from the medical devices 304 and 308-306, and/or the like. As shown in FIG. 3, the device dashboard service 332 includes a graphical user interface (GUI) component 342 that is configured to facilitate display of a GUI 344 on the user device 310 (which may include a display (not shown)). Although the GUI 344 is illustrated as being rendered using a browser 346 running on the user device 310, in embodiments, the GUI 344 may be provided using a client application, a browser plug-in, an application plug-in, application programming interface (API), and/or the like. The GUI 344 may facilitate presenting any number of different types of information to a user, including, for example, device-readiness information; device performance information; clinical event information; configuration information; information associated with software status and/or updates; location information corresponding to medical devices; user information; account information; and the like.

In embodiments, for example, the medical device 304 may be an AED and the GUI 344 may be configured to display the following device information, generated from a self-test report: result of the most recent self-test; device serial number; electrode status/expiration; battery status/expiration; device software revisions; device user ID (if programmed); and/or device self-test interval. A failed self-test may result in the aggregation and display of information such as, for example, integration device "failed" self-test; reason for failed self-test, if applicable; and/or the like.

According to embodiments, the device dashboard service 332 may be configured to cause the GUI component 342 to provide reports that may be displayed using the GUI 344, printed, forwarded, and/or the like. For example, on a periodic basis, the device dashboard service 332 may notify a user of a passed self-test via email, the GUI 344, and/or the like. In another example, a daily, weekly, and/or monthly report may be provided. Additionally, in embodiments, reports, alerts, and/or other types of data may be provided to a user via email, short message service (SMS) messaging, and/or the like.

According to embodiments, the management server 108, 302 may be configured to receive, manage, and present device-readiness information. The device dashboard service 332 may be configured to provide the user with up-to-date information on the readiness of the medical device 304. This information may include: device-readiness (for example, an indication as to whether the medical device 304 passed the latest self-test), electrode expiration/readiness, and battery information (for example, whether the battery contains enough power for a minimum of 1 rescue). According to certain embodiments, the management server 108, 302 may be configured to receive, manage, and present device performance information or data.

According to embodiments, the management server 108, 302 also may be configured to receive, manage, and present clinical event information. The device dashboard service 332 may be configured to provide the user with complete event information once downloaded from the medical device 304. This data may be downloaded in a HIPPA compliant manner. When downloaded the user may be able to view device actions and prompts, along with basic device information in a main screen. From this main screen the user may be able to navigate to additional tabs such as, for example, ECG and CPR analysis. Upon download of clinical event information, the device dashboard service 332 may be configured to provide display of prompts and/or basic information in languages, in which the medical device recorded the data. According to embodiments, the clinical event information may include event logs and device prompt logs, ECG and waveforms; CPR analysis; CPR quality prompts and screens.

The device dashboard service 332 further includes a configuration component 348 configured to provide configuration information to the medical device 304 and/or 308. In embodiments, a medical device 304 may be configurable based on a number of different options that may be selected by a user. The user may be able to configure the medical device 304 by providing user input directly to the medical device 304, by providing configuration information to the medical device 304 via the configuration component 348, and/or the like. In embodiments, for example, the configuration component 348 may receive user input via the GUI 344 to configure various configuration options. The configuration information (including the configured options) may be provided to the medical device 304 using the configuration component 348. In embodiments, for example, configuration information may be provided, in a configuration file, to the medical device 304, which may be configured to read and parse the configuration file, extract the configuration information, and configure itself based on the configuration information. The device dashboard service 332 may enable a user to provide the same configuration information to all medical devices (of a similar type) that the user is managing, unique configuration information to each medical device, and/or various combinations of the above. According to embodiments, the configuration component 348 may provide configuration information that is transmitted over the network 306 to the medical device 304, downloaded to a storage medium (for example, a USB flash drive), and/or the like.

Any number of different options, features, settings, and/or the like, may be configured using configuration information. The types of configuration options, features, and/or settings that are available to be configured by a user may be based on a role assigned to the user, regulatory compliance limitations, safety considerations, and/or the like. In embodiments, for example, the medical device 304 may be an AED, and the configuration options and parameters depicted in Table 1, below, may be available to a user of a first type (for example, a non-administrator), while the configuration options and parameters depicted in Table 2, below, may be available to a user of a second type.

TABLE 1

| | User Configurable Options | |
|---|---|---|
| # | Configurable Option | Possible Values |
| T1 | Lay Rescuer Prompts<br>When this option is checked (On), the unit issues the following voice and text prompts after completion of the power-on self-test and entry into clinical mode: | On<br>Off |

TABLE 1-continued

User Configurable Options

| # | Configurable Option | Possible Values |
|---|---|---|
| | STAY CALM | |
| | CHECK RESPONSIVENESS | |
| | CALL FOR HELP | |
| | Lay Rescuer prompts will only be issued prior to pad placement. If pads are pre-attached the lay rescuer prompts will NOT be issued. | |
| T2 | CPR Countdown Timer | On |
| | The AED Plus 2 will display a visual indication for remaining time in CPR/compression cycle | Off |
| T3 | Language | Language 1 |
| | User configurable for up to three (3) languages | Language 2 |
| | Languages must be individually loaded | Language 3 |
| | Dependent on ordered languages | |
| T4 | Transfer | Transfer via WiFi or USB: |
| | User can: | Clinical event file |
| | Transfer via a USB flash drive or through a WiFi connection. | Device History |
| | | Configuration |
| T5 | Set Time & Date | 00:00 |
| | Allows user to manually set the time on the AED Plus 2 (Ability to set DST) | Month/Day/Year |
| | | DST |
| T6 | CPR Depth Measure of Units | Inches (IN) |
| | | Centimeters (CM) |
| T7 | Lay Breathing Prompt | On |
| | Allows you to configure the "Lay Breathing" prompt of "Open Airway, Check Breathing", based on the guidelines you want to follow. | Off |
| | When disabled (Off), these prompts are not issued. | |

TABLE 2

Administrator Configurable Options

| # | Configurable Option | Possible Values |
|---|---|---|
| 1 | Self Test Interval | 1 day |
| | Sets the period of time between automated self-tests in standby state. | 7 days |
| 2 | Auto Self-Test Report | On |
| | Following the pre-configured self-test the AED Plus 2 will attempt to link with ZOLL Online/En-Pro through a WiFi connection. | Off |
| 3 | CPR Recording | On |
| | When this option is checked (On) and pads with a CPR sensor are attached, the unit performs CPR monitoring, prompts the rescuer, and records chest compressions in the event data file. (Real CPR Help ®). When this option is Off, the unit does the same - BUT does NOT record chest compressions. | Off |
| 4 | Breathe During CPR Prompt | On |
| | The AED Plus 2 will prompt "Give Two Breaths" every 30 recognized compressions | Off |
| 5 | Adult First Shock Energy | 120 J |
| | Sets the energy level in joules for the first shock for an adult patient. | 150 J |
| | | 200 J |
| 6 | Adult Second Shock Energy | 120 J |
| | Note: This value cannot be less than the value selected for the first adult shock. | 150 J |
| | | 200 J |
| 7 | Adult Third Shock Energy | 120 J |
| | Note: This value cannot be less than the value selected for the second adult shock. | 150 J |
| | | 200 J |
| 8 | Pediatric First Shock Energy | 50 J |
| | Sets the energy level in joules for the first shock for a pediatric patient. | 70 J |
| | | 85 J |
| 9 | Pediatric Second Shock Energy | 50 J |
| | Note: This value cannot be less than the value selected for the first pediatric shock. | 70 J |
| | | 85 J |
| 10 | Pediatric Third Shock Energy | 50 J |
| | Note: This value cannot be less than the value selected for the second pediatric shock. | 70 J |
| | | 85 J |
| 11 | No Shock CPR Period | 30 seconds |
| | Sets the duration of the CPR period following a No Shock Advised result for the analysis. | 60 seconds |
| | | 90 seconds |
| | | 120 seconds |
| | | 150 seconds |
| | | 180 seconds |

TABLE 2-continued

Administrator Configurable Options

| # | Configurable Option | Possible Values |
|---|---|---|
| 12 | Post Shock CPR Period<br>Sets the duration of the CPR period following the delivery of a shock. | 30 seconds<br>60 seconds<br>90 seconds<br>120 seconds<br>150 seconds<br>180 seconds |
| 13 | Start with CPR Period<br>Configures the AED Plus 2 to start with CPR once electrodes are attached to the patient. | Off<br>30 seconds<br>60 seconds<br>90 seconds<br>120 seconds<br>150 seconds<br>180 seconds |
| 14 | Continue CPR Prompt<br>"Continue CPR" will be repeated once every N* seconds (see parameter 15) if CPR compressions stop during the CPR interval. When this option is set to Off, the "Continue CPR" prompt will not be issued during the CPR period. | On<br>Off |
| 15 | CPR Prompt Interval<br>This option determines the interval for the following prompts:<br>Real CPR Help ®<br>START CPR<br>CONTINUE CPR | 10 seconds<br>15 seconds |
| 16 | Set Supervisor Passcode<br>Allows user to change the passcode used to enter Supervisor mode | 1 2 3 4 5 6<br>------ |
| 17 | Device Identifier (defaults to SN of device) | Allows input of 11 digit alpha-numeric device ID. |
| 18 | User Transfer via USB or WiFi<br>User can transfer the:<br>Configuration file (device and WiFi settings)<br>Device History Report<br>Clinical Event Data | Transfer via WiFi or USB:<br>Configuration file<br>Device History Report<br>Clinical Event Data |
| 19 | Install (USB)<br>User can install:<br>Configuration file<br>Software upgrade<br>Language file | Install via USB flash drive:<br>Configuration file<br>Software upgrade<br>Language file |
| 20 | Number of Clinical Cases<br>User can configure number of clinical cases the AED Plus 2 will store for both audio and non-audio devices | 1<br>2 |
| 21 | Voice Recording<br>Note: Option will only be available when a customer orders an "AED Plus 2 Pro" device. Default will be "OFF" on enabled devices. | On<br>Off |
| 22 | Device Display<br>Allows user to select information displayed on the LCD during clinical use. | Lay Rescuer<br>ECG and CPR Dashboard<br>ECG<br>CPR Dashboard |
| | Lay Rescuer | Default AED Plus 2 display with animations. |
| | ECG and CPR Dashboard | The AED Plus 2 will display the patient's ECG rhythm and all text prompts. During the CPR cycle the CPR Dashboard will also be active. |
| | ECG | The AED Plus 2 will display the patient's ECG rhythm and text prompts. |
| | CPR Dashboard | Text prompts will be displayed. During the CPR Cycle the CPR Dashboard will also be active. |

As shown in FIG. 3, the device dashboard service 332 may also include an update component 352 configured to provide software updates to the medical device 304. According to embodiments, the update component 352 may provide software updates that are transmitted over the network 306 to the medical device 304, downloaded to a storage medium (for example, a USB flash drive), and/or the like. Additionally, the update component 352 may be configured to enable scheduled software updates, periodic software updates, and/or the like.

In embodiments, the device dashboard service 332 may include a customer registration wizard 350 configured to assist a user in registering to use one or more services provided by the management server 302. The customer registration wizard 350 may be configured to walk a user through a registration process, gather various types information from the user, and send the information to various appropriate services, databases, entities, and/or the like. For example, the registration wizard 350 may solicit, and/or facilitate the creation of, login credentials corresponding to a particular user device, user, organization, medical device, group of medical devices, user account, and/or the like. These login credentials may be provided to a first service and/or entity. The registration wizard 350 may be configured to solicit, and/or facilitate the creation of, account set-up information, which may be provided to a second service and/or entity. Additionally, for example, the registration wizard 350 may be configured to solicit device warranty registration information, which may be provided to a third service and/or entity. Any number of different types of information may be requested from a user and/or generated during a registration procedure and the registration wizard 350 may facilitate providing any number of different types of information to any number of different service and/or entities.

During a registration process, a user may configure any number of various aspects, features, options, and/or the like, associated with the device dashboard service 332. In embodiments, for example, a user may be able to specify a notification frequency, which may be a frequency with which the medical device 304 is configured to communicate information to the management server 302. The device dashboard service 332 may, in embodiments, facilitate tiered device management, grouping medical devices based on geography, selection of the language to be used, providing portals for distribution partners, and/or the like.

According to embodiments, the device dashboard service 332 may facilitate user role-based permissions. That is, in embodiments, each user associated with a particular account, group of medical devices, and/or the like, may be assigned a particular role that defines the level of access the user has to various types of information, functionality, and/or the like. The device dashboard service 332 may also identify responsibilities of each user and implement mechanisms for tracking their relative performance, regulatory compliance, internal policy compliance, and/or the like. In embodiments, the device dashboard service 332 may be configured to manage a number of different user types associated with each type of medical device.

As an example, the device dashboard service 332 may be configured to recognize various types of users associated with AEDs. That is, for example, the device dashboard service 332 may recognize five main user roles associated with AED devices themselves: AED Maintainer; AED Program Manager; AED Rescuer; Medical Director; and Medical Doctor. Although these user roles associated with AEDs are described herein for the purposes of clarity and illuminating possible implementation concepts, embodiments of the invention facilitate supporting any number of different user roles associated with any number of different types of medical devices.

According to embodiments, an AED Maintainer may be tasked with maintaining a fleet of AEDs (for example, 1-100+AEDs). The AED Maintainer may be responsible for ensuring that all AEDs are in working order, are up to date, have current electrodes and batteries, and/or the like. An AED Program Manager may, for example, be tasked with managing a number of locations at which an AED Maintainer is present. The AED Program Manager may have responsibility over an entire AED Program (corporate/school district/military base, and the like), ensuring that all locations are meeting internal and external requirements. In embodiments, the AED Program Manager may be provided the ability to view information associated with all AEDs for which he or she is responsible through a hierarchical system. The AED Rescuer may operate the AED during a clinical patient event.

In embodiments, the Medical Director may provide medical direction over a number of AEDs. The Medical Director's responsibilities may include, for example, ensuring that all of the AEDs under the Medical Director's care are properly maintained; ensuring that all AED sites have up-to date CPR/AED Certified responders; providing post-event support and/or clinical event data review. Thus, for example, the Medical Director may be provided the ability to quickly view locations that they are in charge of managing to confirm compliance with various aspects of AED management, such as, for example, to confirm device-readiness and the preparedness of a location to respond to a medically emergent situation. Additionally, in embodiments, the Medical Doctor may be provided with the ability to view clinical event information closely following the clinical use of an AED.

Similarly, the device dashboard service 332 may be configured to recognize a number of dashboard user roles. For example, in embodiments, dashboard users may have responsibility over the management and maintenance of an AED or multiple AEDs. Additionally these users may have responsibility for the download and/or review of clinical event information. In embodiments, these users may be assigned one or more of four user roles: administrator, site-user, medical director/doctor, and EMS Agencies.

For example, an administrator may be responsible for the management of multiple AEDs spread over multiple locations. The locations may vary (for example, by state, country, town, or the like) with each site having a specific responsible user. The administrator may be responsible for the management of all sites, groups of sites, and/or the like. Illustrative activities related to an administrator's responsibility may include ensuring compliance with "Good Samaritan" laws, ensuring AED program compliance, ensuring device-readiness, providing CPR/AED training, and facilitating device configuration. In embodiments, the administrator's primary task may not involve AED device management, as the management of an AED program may be an assigned task.

In embodiments, a site-user may be responsible for all AEDs associated with an individual location. The site user may report to an administrator as their site could be one of multiple locations associated with one customer. Illustrative activities related to a site-user's responsibility may include ensuring device-readiness, device performance, training of an emergency response team, and/or the like. A medical director/doctor may have responsibility over multiple AEDs at multiple locations, and may be a prescribing physician. The medical director/doctor may be responsible over AEDs deployed in multiple locations. They may be responsible for ensuring that all sites maintain their AEDs properly and are compliant with training certifications. Additionally, the medical director/doctor also may provide post-event support and may review clinical event information. Illustrative activities related to a medical director/doctor's responsibilities may include tracking individual site compliance, providing post-event support, review of clinical event information, and/or the like. Additionally, in embodiments, EMS Agencies may also be an "administrator" if the EMS service offers a Public Access Defibrillation (PAD) program. Additionally, the device dashboard service 332 may be configured to integrate into EMS response software, for example, to alert dispatchers of the locations of AEDs in close proximity to a cardiac arrest emergency.

According to embodiments, the management server 302, the medical device 304, the user device 310, and/or another system component such as, for example, an administration system (for example, the administration system 542 depicted in FIG. 5), may be configured to process information received from the medical device 304 and, in embodiments, utilize the information and/or processed information to facilitate additional services. For example, in embodiments, any one or more of device-readiness information, device performance information, and clinical event information may be processed to generate statistical reports across geographic areas, customers, devices within a fleet, device types, devices of certain ages, versions, and/or configurations, environmental conditions (for example, elevation, average temperature, temperature ranges, average humidity, humidity ranges, average barometric pressure, barometric pressure ranges, sun-exposure levels and/or durations, atmospheric contaminant types and/or levels, and/or the like), use conditions (for example, frequency of use, nature of use, durations of use, and/or the like), user demographics (for example, user roles, user types, user ages, user experience levels, and/or the like), outcomes (for example, measures of intervention success, prognosis, diagnosis, and/or the like), and/or the like. Reports may be generated periodically, manually, automatically, and/or the like, and may be provided to any number of devices, users, groups of users, regulation authorities, clinicians, and/or the like.

In embodiments, the management server 302, the medical device 304, the user device 310, and/or another system component such as, for example, an administration system (for example, the administration system 542 depicted in FIG. 5), may be configured to facilitate any number of other functionalities, services, and/or features associated with managing a fleet of medical devices. For example, a user may be able to remotely access audio/video equipment associated with the medical device 304, facilitate medical billing and/or other financial transactions, respond to requests for medical information, obscure personally identifiable information, and/or the like.

The illustrative operating environment 300 shown in FIG. 3 is not intended to suggest any limitation as to the scope of use or functionality of embodiments of the present invention. Neither should the illustrative operating environment 300 be interpreted as having any dependency or requirement related to any single component or combination of components illustrated therein. Additionally, any one or more of the components depicted in FIG. 3 may be, in embodiments, integrated with various ones of the other components depicted therein (and/or components not illustrated), all of which are considered to be within the ambit of the present invention. For example, a web server (which may include one or more components, features or aspects of the management server 302) may be integrated with the medical device 304, may be accessible by the browser 346, and may be used to manage one or more other medical devices 308. Embodiments of situations in which a medical device 304 includes a web server, in this manner, are disclosed, for example, in U.S. Publication No. 2014/0266794, "PATIENT MONITOR SCREEN AGGREGATION," filed by Brown et al. on Mar. 14, 2014, the entirety of which is hereby incorporated by reference herein, for all purposes.

Figure 4:
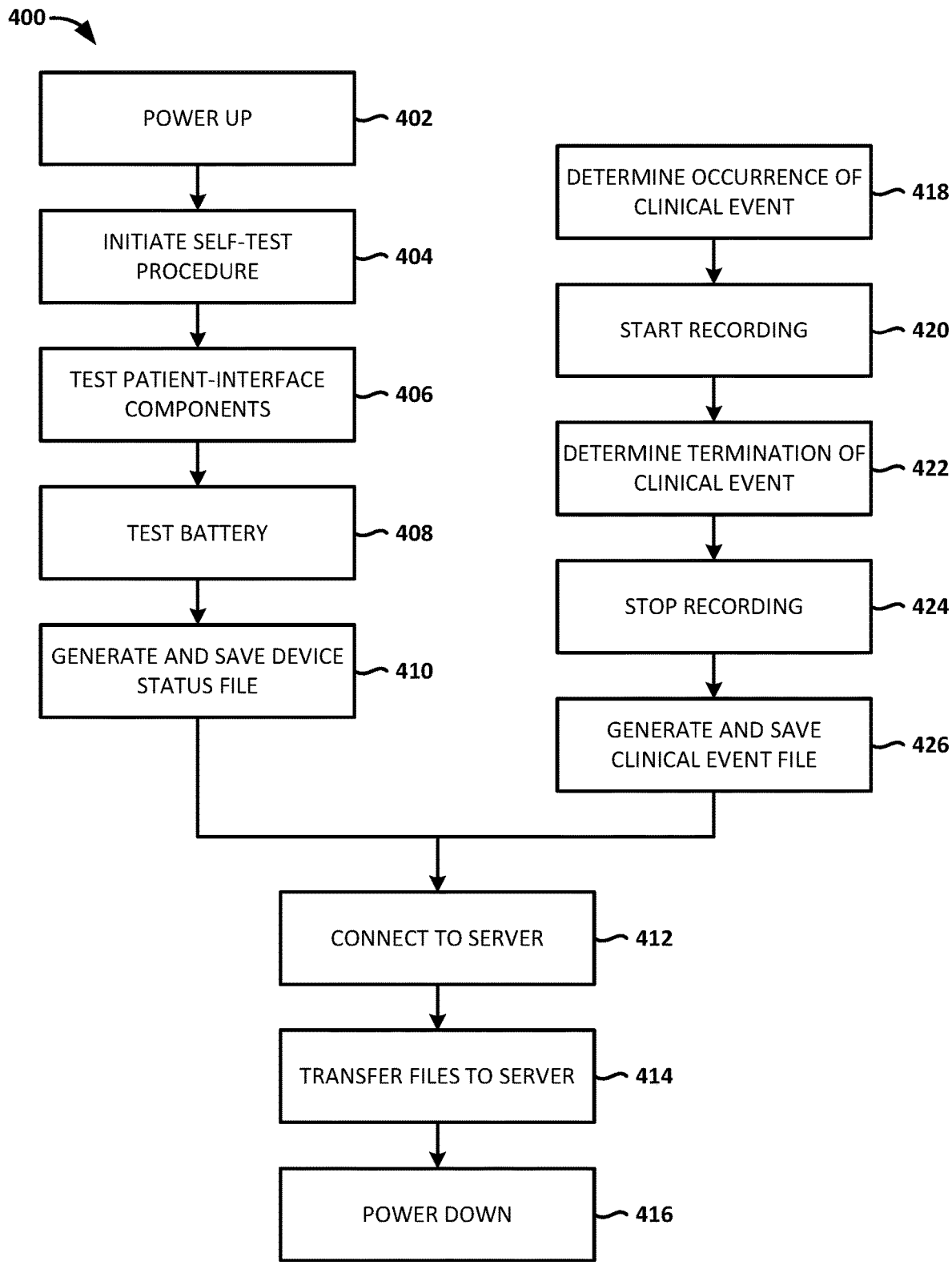
FIG. 4 is a flow diagram depicting an illustrative method of medical device management in accordance with embodiments of the disclosure.

As described above, embodiments of the invention provide a management server configured to facilitate remote management of a number of medical devices and/or information received therefrom. FIG. 4 is a flow diagram depicting an illustrative method 400 of facilitating medical device management in accordance with embodiments of the invention. As shown in FIG. 4, embodiments of the method 400 may be performed by a medical device (for example, the medical devices 102, 104, and/or 106 depicted in FIG. 1; and/or the medical devices 304 and 308 depicted in FIG. 3) and may include powering up (block 402) and initiating a self-test procedure (block 404). In embodiments, the medical device may be configured to initiate the self-test procedure periodically, according to a programmed schedule; upon to installation of a battery or batteries; upon being powered up (i.e., turned on); upon receiving a user input; and/or the like.

In embodiments, the self-test procedure may be configured to test any number of different functions, features, and/or the like. As shown in FIG. 4, the illustrative method 400 includes testing patient-interface components (block 406) and testing the battery (or batteries) (block 408). Using the device-readiness information resulting from the self-test procedure, a device status file is generated and saved in a local memory component (block 410). According to embodiments, the self-test procedure may include any number of different protocols and procedures for verifying the ability of patient-interface components, batteries, communication components, and/or the like, to operate safely and effectively when needed.

According to embodiments, patient-interface components may include any type of component configured to facilitate an interaction with a patient such as, for example, therapy-delivery components, sensing components, communication components, and/or the like. For example, in the case of a medical device that is, or includes, an AED, the self-test procedure may include verifying that the defibrillation electrodes are properly connected to the device; verifying that the ECG signal acquisition and processing electronics are functional; verifying that the defibrillator electronics are functional and can charge and discharge at a predetermined level; verifying proper function of the microprocessor electronics and the integrity of the software; verifying that the CPR monitoring and compression depth detection are functional; verifying that voice prompts and/or visual indicators are functional; verifying that adequate battery capacity remains; verifying that the defibrillation electrodes have adequate usable life remaining; and/or the like.

As shown in FIG. 4, the method may further include connecting to a server (block 412), and transferring files to the server (block 414). The server may be, or be similar to, for example, the management server 108 and/or the collection server 116 depicted in FIG. 1, and/or the management server 302 depicted in FIG. 3. Optionally, the medical device may be configured to power down (block 416) after transferring the files to the server. Embodiments of the illustrative method 400 may also include determining the occurrence of a clinical event (block 418) and, in response to determining the occurrence of the clinical event, start recording (block 420). In embodiments, the medical device may be configured to record any number of different types of clinical event information such as, for example, heart rate, blood pressure, temperature, respiration rate, blood oxygen level, end-tidal carbon dioxide level, pulmonary function, blood glucose level, weight, electrocardiographs, and/or the like. The medical device determines when the clinical event has terminated (block 422), stops recording (block 424), and generates and saves a clinical event file (block 426). The clinical event file, containing clinical event information, may be transferred to the server (block 414) along with the device status file, in a separate communication, and/or the like.

FIG. 5 is a schematic block diagram depicting an illustrative operation of an operating environment 500 in accordance with embodiments of the invention. As shown in FIG. 5, the operating environment 500 includes a medical device 502 (for example, an AED) that is communicably coupled to a collection server 504. The medical device 502 may be (or be similar to), for example, the medical devices 102, 104, and/or 106 depicted in FIG. 1, and/or the medical devices 304 and/or 308 depicted in FIG. 3; and the collection server may be (or be similar to), for example, the collection server 116 depicted in FIG. 1. In embodiments, the medical device 502 may be configured to perform periodic self-tests to evaluate the condition of one or more batteries, one or more patient interface components (for example, electrodes), and/or the like. The results of the self-tests may be stored, as device-readiness information, in a local memory on the medical device 502. The device-readiness information may include, for example, the date and time of the self-test, the type of self-test performed, and/or the results of the self-test.

The medical device 502 is configured to communicate the device-readiness information 506, as well as clinical event information 508, to the collection server 504, which may be, for example, a software-as-a-service (SaaS) implementation hosted on the cloud, independent of the geographical site of the medical device 502. The medical device 502 may also communicate, to the collection server 504, performance data, maintenance logs, a device identifier (ID), a device serial number, and/or the like. In embodiments, the medical device 502 may include a global positioning system (GPS), or other location-identifying technology, and may communicate location information to the collection server 504. In other embodiments, the medical device 502 does not include a GPS or other location-identifying technology, in which case no location information is communicated to the collection server 504. In embodiments, a device ID may be configured to include, within its text, information about the location of the medical device 502. In embodiments, the various types of information may be sent from the medical device 502 to the collection server as a Device History File (DHF) 510. The DHF 510 may be, for example, a file configured using a proprietary file format and communicated over standard HTTP/SSL. According to embodiments, the DHF 510 may be configured using any number of different formats and may be communicated using any number of different communication protocols.

According to embodiments, the medical device 502 may initialize communication with the collection server 504 in any number of various ways. For example, the medical device 502 may initiate communication manually (for example, in response to user input to the medical device 502), automatically (for example, according to a predetermined schedule, in response to an event, etc.), and/or the like. In an automatic configuration, the medical device 502 may be configured to attempt to initiate a session with the collection server 504 periodically, upon receiving the DHF 510, and/or according to any other configured schedule. In embodiments, if the medical device 502 fails to establish communication with the collection server 504, it may be configured to re-attempt communication initiation a certain number of times before powering down and waiting to attempt to initiate communication again according to the schedule.

As shown, the collection server 504 includes a communication component 512 that is configured to receive the DHF 510 from the medical device 502, a parsing component 514 that is configured to parse the DHF 510, and an indexing component 516 that is configured to save the parsed information 518 in a database 520. The database 520 may include a relational database, a tabular database, a multidimensional data cube, and/or the like. Additionally, the database 520 may represent one or more databases distributed across one or more memory components, computers, and/or the like. According to embodiments, the collection server 504 may be configured to interrogate the medical device 502 and/or may maintain a registry of medical devices with which it communicates; while, in other embodiments, the collection server 504 does not interrogate medical devices and/or does not maintain a registry of medical devices with which it communicates. Information associated with a particular medical device 502 may be indexed according to the device ID and/or serial number corresponding to that medical device 502. In embodiments, the collection server 504 may continue to build the database 520 without purging information contained therein, while in other embodiments, the collection server 504 may continuously or periodically purge information from the database 520 to make room for new information.

As shown in FIG. 5, the operating environment 500 also includes a management server 522, which may be configured to facilitate user access, via a user device 524, to information obtained from the medical device 502. The management server 522 may be (or be similar to) the management server 108 and/or the collection server 116 depicted in FIG. 1, and/or the management server 302 depicted in FIG. 3. In embodiments, the management server 522 facilitates remote maintenance, monitoring, and/or management of various medical devices 502. In the illustrated embodiments, the management server 522 does not communicate directly with the medical device 502, but receives information from the medical device 502 only through the collection server 504. In other embodiments, the management server 522 may be configured to communicate directly with the medical device 502.

The management server 522 may be configured to obtain information from the medical device 502, via the collection server 504, in any number of different ways. For example, the management server 522 may include a query component 526 configured to obtain indexed information 528 via a specific query (for example, a device-specific query). The query component 526 may be configured to query the database 520 in response to user input (received, for example, via the user device 524), automatically, according to a configured option, and/or the like. In embodiments, the collection server 504 may be configured to send indexed information 528 from the database 520 to the management server 522 according to a configured option such as, for example, anytime information is received by the collection server 504, periodically, anytime information associated with a failed self-test is received, and/or the like. To facilitate reliability, the management server 522 and/or the collection server 504 may be configured to provide an alert to the user device 524 in the event that information that is expected to be received about a particular medical device 502 is not received. This alert may be provided in the form of email, pop-up screens, and/or the like.

The management server 522 may include a device dashboard 530 that is configured to provide a graphical user interface (GUI) 532 with which a user can interact via the user device 524. The device dashboard 530 may be configured to interact with a database 534 to store, retrieve, and/or manipulate account information 536 associated with a particular user, user device, fleet of medical devices, and/or the like. In operation, for example, the user logs into the service provided by the device dashboard 530 using a username and password and is provided with information associated with medical devices 502 registered to that user. The device dashboard 530 may be configured to allow a customer to register medical devices, view a dashboard feature that presents overall compliance (for example, maintenance status of all registered medical devices), log maintenance checks, and view and edit information about medical devices and the sites in which they are located. In embodiments, the management server 522 provides a role-based system for device management corresponding to various sites at which the medical devices are located.

As is further shown in FIG. 5, the illustrative operating environment 500 includes an integration component 538 that is configured to facilitate interaction between the database 520 and one or more systems or devices. For example, as shown, the integration component 538 may be configured to provide indexed information (for example, clinical event information) 528 to an electronic medical record (EMR) system 540, an administration system 542, and/or the like. The EMR system 540 may be any EMR system, combination of EMR systems and/or the like. In embodiments, the administration system 542 may be a system configured to administer one or more aspects of embodiments of the illustrative operating environment 500. For example, the administration system 542 may be associated with an entity that manages, hosts, and/or otherwise provides the management server 522, the collection server 504, and/or the medical device 502, and/or the like. Embodiments of the administration system 542 may facilitate quality control, software updates, configuration updates, legal compliance, and/or the like.

The illustrative operating environment 500 shown in FIG. 5 is not intended to suggest any limitation as to the scope of use or functionality of embodiments of the present invention. Neither should the illustrative operating environment 500 be interpreted as having any dependency or requirement related to any single component or combination of components illustrated therein. Additionally, any one or more of the components depicted in FIG. 5 may be, in embodiments, integrated with various ones of the other components depicted therein (and/or components not illustrated), all of which are considered to be within the ambit of the present invention.

FIG. 6 depicts an illustrative data sharing system 600 including one or more medical devices in accordance with embodiments of the present invention. As shown in FIG. 6, each of the medical devices 602/604 is provided with a processor 608, a memory 610, and a display 612. In certain embodiments, one or more of the medical devices 602/604 can be a patient monitor defibrillator or an automated external defibrillator. Further, each of the medical devices 602/604 can optionally be provided with one or more batteries 614 for power. In addition, as noted above with reference to FIG. 3, each of the medical devices 602/604 can be provided with a patient-interface component (not shown) such as one or more defibrillation electrodes (pads), one or more infusion needles, and/or the like. Each of the medical devices 602/604 may also be provided with a processor 608. The processor 608 is configured, for example, with a communication component 618 to provide communication between the medical devices 602/604, and/or a cloud-based network 606 which may be unidirectional or bidirectional. Thus, the medical device 602 can communicate directly with the medical device 604 (and vice versa), or can communicate with the medical device 604 via the cloud-based network 606.

Either of the medical devices 602/604 may be used during the first part of an emergency medical event. In certain instances, the second part of the emergency medical event occurs after the first part of the emergency medical event. For example, the first part of an emergency medical event may be characterized as that in which a first responder (such as person having little or no training in emergency response situations) assists a patient. In other instances, the first part of an emergency medical event may be characterized as a trained medical device personnel responding to an emergency medical event. Either of the medical device 602 and the medical device 604 may be used in a second part of an emergency medical event. The second part of an emergency medical event may be characterized, for example, as a situation where an EMT engages in the emergency medical event after a first responder, or a physician at a hospital engages in the emergency medical event after the EMT and/or first responder.

In a potential emergency medical event, the (first) medical device 602 is configured to monitor a patient and store first clinical information in its memory 610 (and such memory may be on device 602, on a networked device, or both, and/or distributed across multiple devices including device 602 or not including device 602). The (second) medical device 604 is configured to monitor the patient and store second clinical information about the patient in its memory 610 (and such memory may be on device 602, on a networked device, or both, and/or distributed across multiple devices including device 602 or not including device 602). A control module 616 is provided with or for the (first) medical device 602 and the (second) medical device 604, or optionally with or for the cloud-based network 606. The control module 616 provided with the (second) medical device 604 is configured to receive an indication that the (first) medical device 602 and the (second) medical device 604 are to be used on the same patient during the same emergency medical event. This indication is discussed in further detail with reference to FIG. 7. Based on the indication, access is established by the (second) medical device 604 to the first clinical information as stored on the (first) medical device 602. As a result of this access, the (second) medical device 604 is permitted to display, on its display 612, at least some of the first clinical information during the emergency medical event. In addition, the (second) medical device 604 can also modify operation of the (second) medical device 604 based on the first clinical information. Further, yet, the (second) medical device 604 may also store the first clinical information in the memory 610 of the (second) medical device 604. The (second) medical device 604 can also communicate the first clinical information to a remote database via the cloud-based network 606.

The control module 616 is also configured to provide access for the (second) medical device 604 to memory 610 provided with the (first) medical device 602. In certain embodiments, the clinical information can be stored, respectively, by the (first) medical device 602 and the (second) medical device 604 in a first memory and a second memory. The first memory and the second memory can be part of a same memory device (such as memory 610 shown in FIG. 6). In certain embodiments, the first memory 610 is provided on the (first) medical device 602 and the second memory 610 is provided on the (second) medical device 604. The cloud-based network 606 can also include first and second memory that stores the clinical information. In such an embodiment, the (first) medical device 602 and the (second) medical device 604 are wirelessly communicably coupled via the cloud-based network 606.

In certain embodiments, the medical devices 602/604 are also configured to communicate data indicative of the devices' clock. In this manner, the medical devices 602/604 are able to coordinate data transmission such that collected and logged data will include the same reference clock.

Syncing of each of the medical devices 602/604 clocks minimizes potential errors by way of missing or duplicative data entries. For further discussion on time-stamping and syncing of device clocks, reference may be made to U.S. Publication No. 2013/0049956, published on Feb. 28, 2013, the entirety of which is hereby incorporated by reference herein, for all purposes.

As noted above, the medical devices 602/604 can wirelessly communicate directly between each other, and can also wirelessly communicate via the cloud-based network 606. In this manner, a web server can also access the cloud-based network 606. Further, the medical devices 602/604 can also include a web browser. Thus, communication can occur between one or more of the medical devices 602/604 and the web server via the cloud-based network 606. In this manner, a trained professional connected at the web server can guide a lay person through responding to a medical emergency event via the web browser provided with one or more of the medical devices 602/604. For further discussion of a websocket connection that can be provided to allow for connection between the web server and the web browser are disclosed, for example, in U.S. Publication No. 2014/0266794, "PATIENT MONITOR SCREEN AGGREGATION," filed by Brown et al. on Mar. 14, 2014, the entirety of which is hereby incorporated by reference herein, for all purposes.

Figure 7:
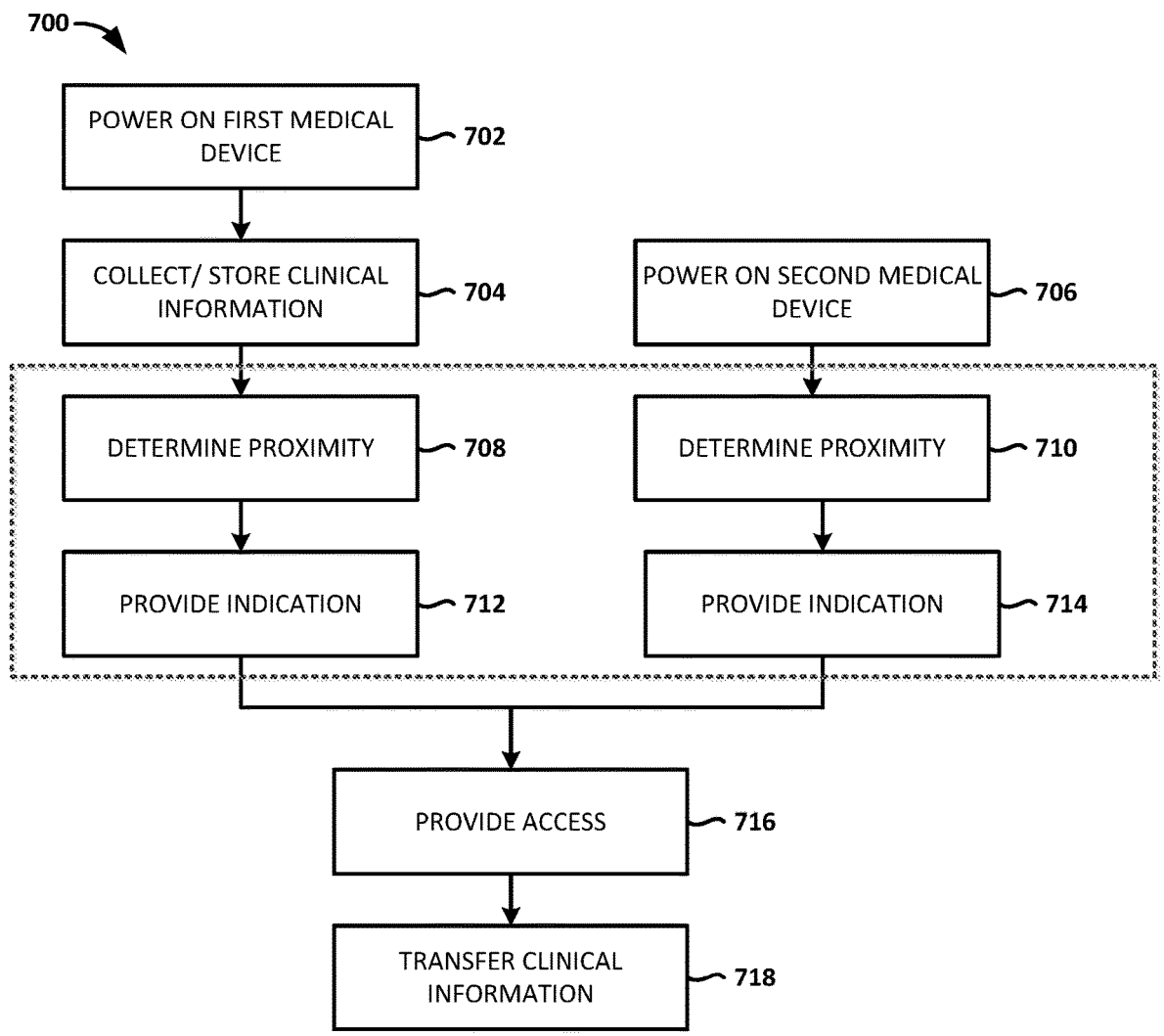
FIG. 7 is a flow diagram depicting an illustrative method of data handoff from one or more medical devices in accordance with embodiments of the present disclosure.

FIG. 7 is a flow diagram 700 depicting an illustrative method of data handoff from one or more medical devices in accordance with embodiments of the present invention. As shown at block 702, a first medical device is powered-on. This may occur during an emergency response situation remotely or during an emergency response situation at a hospital. As is shown at block 704, the first medical device collects and stores clinical information through monitoring a patient. As is shown at block 706, a second medical device is powered-on. At this point, proximity of the first medical device and second medical device is determined as is shown at blocks 708 and 710. The proximity of each of the medical devices can be determined in a number of ways, and is provided as a safeguard in determining that each of the medical devices are provided at the same location and operable on the same patient. For instance, in certain embodiments, the medical devices will determine proximity (including, for example, use of a control module described above with reference to FIG. 6) in response to exchange of Bluetooth or other radio frequency signals. In other embodiments, proximity of the medical devices is determined in response a receipt of a global positioning system (GPS) signal from each of the first medical device and the second medical device. Further, in other embodiments, proximity can be determined in response to each of the first medical device and the second medical device being connected to a shared local area network (LAN).

As is shown at blocks 712 and 714, in response to a determination that the medical devices are proximate one another, one or more of the devices will prompt an indication to occur. The indication can occur visually on the medical devices' display or auditory from a speaker provided with the devices. The indication for confirmation ensures that the medical devices are authenticated for connection. Authentication can mean that both medical devices are collecting data and/or operating on the same patient. If the devices were not operating on the same patient, the exchange of clinical information may not provide an intended function. Further, more than two medical devices may be present at an emergency event (or hospital). Thus, the indication allows for a check by the device operators that the correct clinical information will be exchanged. Such an indication can be a visual code (e.g., both devices showing the same combination of lights or colors of lights), a visual beacon such as a picture, a visual light such as both devices showing the same colored light, a prompt for a key-code, an audible prompt, and/or a patient specific input such as scanning the patient's fingerprint or driver's license or other unique identifying information to ensure that the correct clinical data is exchanged between devices.

The medical devices will provide access, as is shown at block 716, after the indications are matched on the medical devices. The dotted line surrounding blocks 708-714 represents an authentication stage of pairing the two medical devices. If the devices are not proximate to one another, or the indication is not matched, the medical devices will not pair, and access will not be provided. Subsequently, the transfer of clinical information can occur, as is shown at block 718.

In addition to or instead of the device pairing that can occur as described above, handoff of clinical event data accomplished via a remote server or the "cloud" may also occur automatically and/or with or without pairing or other intervention by the users of the medical devices. Data relating to a patient may be gathered by a first device 102 and made available or stored on a server (e.g. server 108 and/or 116). The data set includes one or more indications or fields or other associations that identify the patient, identify the time that the data set was collected, that identify the location where the data set was collected, and/or that identify the person or crew member(s) associated with the data collection or data entry. When a second device 104 is intended to be used on the same patient during the same medical event, for example, the second device 104 may query the remote server by sending to the remote server one or more of: information that identifies the patient, information about the time (e.g. that the query is being made to the server), information about the location of the second device 104, and/or information that identifies the person or crew members associated with or who are using the second device 104. The server (e.g. 108) may attempt to match one or more such data points or types of information with stored clinical event data. When the server identifies a match, the server takes the stored clinical event data (from the first device 102) and sends it to the second device 104. The patient information may include the patient's name, social security number, driver's license number, or any other uniquely identifying information about the patient, and such information may be input automatically and/or manually for querying the server (e.g. via the first device 102 and/or the second device 104 or some other device). Location information may be supplied by GPS or other navigation or positioning system. Crew identity information may be supplied by manual data entry or automatically (e.g. via radio frequency identification), and time information by be provided by a clock or clock signal.

In other words, if data received by the server from device 102 indicates a patient P, a time T, a location L, and a crew member C for a clinical data set, and if device 104 queries the server indicating that it is being used on patient P at time T, or at time T and location L, or by crew member C at time T, the server may, based on this match, send the clinical data set to device 104 to complete the handoff. Alternatively, such a match may be identified by any one or more correlations with P, T, L, C, or other elements within the data set. Even if an exact match or a direct correlation is not observed by the server, the server may identify a correlation that is strong enough to permit the data from device 102 to be sent to device 104, for example a data set collected from patient P at a time T that was two hours prior to the time indicated by device 104 at which device 104 is being used to treat the same patient P. As an alternative to querying of data sets, the server itself may be able to determine whether two devices are being used on the same patient at roughly the same time, by observing its communication traffic. Alternatively, the server may be configured to identify the necessary correlation by comparing the clinical data sets themselves and determining whether correlations between the data sets are strong enough to indicate that they uniquely identify a particular patient. This may be accomplished with neural networks, learning algorithms, dataset comparisons, and other data analysis methods known in the art. For example, a patient's ECG signal at time T1 observed by device 102 might be so similar to the patient's ECG signal at time T2 observed by device 104 that the server recognizes that the two devices 102 and 104 are or have been used on the same patient around the same time, and thus initiate (e.g. automatically and/or after confirmation) the transfer of clinical event data collected by one device to the other device and/or vice versa.

As discussed herein, the clinical information can be transferred using protocols such that devices of different manufactures are compatible. Such a protocol can include NEMSIS, or any other type of data standard for hospitals or emergency medical data or the like.

As further illustrated in FIGS. 6 and 7, clinical data may be handed off from a first medical device 602 to a second medical device 604 during a medical event, such as, for example, an emergency medical event. This may be done directly device-to-device, and/or via a network 606. The instructions and/or processing resources for carrying this out may be included in one of, or a combination of two or more of, the first medical device 602, the second medical device 604, a server (e.g. 302) in the network 606, and a database (e.g. 336) otherwise communicably coupled to the network 606, according to embodiments.

In some embodiments, the first medical device 602 is attached to or communicably coupled to a patient, and generates, gathers, and/or records clinical information about the patient during the medical event. When a second medical device 604 is used to monitor the patient during the same medical event, for example when an AED is used with the patient initially, and later an EMS crew arrives with an ALS monitor/defibrillator which is then substituted for the AED, the fact that the second medical device is intended to be used on the same patient during the same medical emergency is indicated and/or confirmed. This may be done via a visual indication on one or both screens of the first and second medical devices, and/or via an audio signal or other pairing mechanism. This ensures that any clinical data gathered by the first medical device is associated and displayed or used with the correct second medical device, according to embodiments.

Once the association between the appropriate first medical device and the appropriate second medical device is confirmed, one or more of the following may be conducted during the medical event (the same medical event):
 (a) displaying at least some of the clinical information on the second medical device (e.g. on display 322),
 (b) displaying on the second medical device information derived from at least some of the clinical information,
 (c) modifying operation of the second medical device based on the clinical information, and
 (d) storing the clinical information in the second medical device or a remote database (e.g. 336).

According to some embodiments, two or more of these four items may be conducted during the medical event, or three or more, or all four, in addition to and/or instead of other items.

In some cases, the clinical information is generated during a first part of the medical event (e.g. when the patient is experiencing symptoms, prior to the patient entering cardiac arrest or during cardiac arrest), and the second medical device is used to monitor the patient during a subsequent part of the medical event. Displaying on the second medical device information derived from at least some of the clinical information may include displaying, on the second medical device, one or more of (and/or two or more of or three or more of) displaying a representation of a heart rhythm presenting at a time when the first medical device began monitoring the patient, displaying a representation of a heart rhythm presenting at a time immediately prior to the patient going into cardiac arrest, and displaying a representation of a heart rhythm of the patient at a time subsequent to administration of a shock to the patient's heart. Often, when EMS technicians or medics arrive at the scene of a medical emergency in which the patient has entered cardiac arrest, they are often unable to determine what the presenting rhythm was, which heart rhythm caused or immediately preceded the cardiac arrest, and/or how the heart rhythm responded after one or more shocks (in situations where an AED was used with the patient). Pairing the second device with the first device (e.g. AED) and permitting the second device to use the clinical information gathered by the first device in the ways described herein allows the EMS technicians to review this information with the second device, modify or inform clinical decision support or other algorithms used by the second device, display on the second device information derived from the clinical data, and/or store the clinical data in the second device and/or in a remote database (e.g. 336), according to embodiments of the present invention.

In some cases, the confirmation that the second medical device is to be used on the patient during the medical event further includes providing an indication on at least one of the first medical device and the second medical device that the first medical device and the second medical device are proximately located. This may occur via the exchange of radio frequency signals, for example beacon-type or other proximity signals.

According to some embodiments, the clinical information details administration of cardiopulmonary resuscitation (CPR) to a patient during the medical event. Such clinical information about CPR may include information about CPR quality, such as chest compression metrics, and/or an indication of CPR time, including one or more of beginning time of CPR administration, ending time of CPR administration, duration of CPR administration, and chest compression timing. Without such clinical data hand off from an AED to an ALS monitor/defibrillator, the EMS technicians are often unable to determine whether CPR was performed and whether the CPR quality was low or high. Even if such data is gathered by the AED or other intermittently used medical device, such devices are often unable to present or display such information or such information in any level of depth that is useful during the same emergency. Being able to view or use this clinical data with the second medical device even though the second medical device was not itself used to collect the clinical data earlier in the same emergency permits the EMS technicians to make better decisions about the types and timing of additional treatment protocols, according to embodiments. Also, being able to hand off the ECG or other clinical data permits the EMS technicians to save valuable time by not having to take a new set of clinical data for a certain time period before making further decisions.

Such considerations and functionality described above may also apply equally to a clinical data handoff between, for example, an ALS monitor/defibrillator and a hospital-based monitor/defibrillator, according to embodiments of the present invention. For example, clinical data may be handed off from an AED to a portable ALS monitor/defibrillator, and then additional clinical data may be generated and added to the first clinical data, with both sets of clinical data then being handed off from the ALS monitor/defibrillator to the stationary or hospital-based or other additional monitor/defibrillator. In such scenarios, the attending physician at the hospital is able to view or use, on one or more devices in the hospital setting, the clinical information first gathered by the AED at the beginning of the medical event.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

What is claimed is:

1. A system for handoff of clinical data, the system comprising:
   a first medical device comprising an automated external defibrillator (AED) configured to:
      monitor and deliver therapy to a patient during a first part of a medical event when the first medical device is attached to the patient,
      collect first clinical information from the patient during the first part of the medical event, and
      store the first clinical information about the patient;
   a second medical device comprising an advanced life support (ALS) monitor/defibrillator configured to:
      monitor and deliver therapy to the patient as a substitute for the first medical device during a second part of the medical event when the second medical device is attached to the patient, wherein the second part of the medical event occurs after the first part of the medical event,
      collect second clinical information from the patient during the second part of the medical event, and
      store the second clinical information about the patient; and at least one control module configured to:
   prompt for a confirmation by a device operator at both of the first and second medical devices that the first and second medical devices are to be used on the patient during the medical event,
   determine that the first and second medical devices are to be used on the patient during the medical event based on an identified match or correlation between (a) first patient specific input provided at the first medical device by the device operator, wherein the first patient specific input to the first medical device comprises one or more of a patient's name or a patient identification number, and (b) second patient specific input provided at the second medical device by the device operator, wherein the second patient specific input to the second medical device comprises one or more of the patient's name or the patient identification number,
   establish a communicative coupling between the first medical device and the second medical device,
      wherein establishing the communicative coupling comprises cloaking a network identifier of the second medical device,
      wherein establishing the communicative coupling further comprises causing the first medical device to request the communicative coupling with the second medical device using the network identifier of the second medical device, and
      wherein the network identifier of the second medical device is stored in a first memory of the first medical device before establishing the communicative coupling,
   determine that the first and second medical devices are proximately located based on establishing the communicative coupling, and
   based on both of (a) the confirmation that the first and second medical devices are to be used on the patient during the medical event, and (b) determining that the first medical device and the second medical device are proximately located, enable handoff of the first clinical information stored by the first medical device to the second medical device,
   wherein, in response to the handoff, the second medical device is configured to:
      (a) display, at the second medical device, at least some of the first clinical information during the second part of the medical event after the second medical device has been substituted for the first medical device, the second part of the medical event being when the second medical device is attached to the patient, wherein the first medical device collected the first clinical information during the first part of the medical event when the first medical device is attached to the patient prior to the second medical device having been substituted for the first medical device, and
      (b) display, at the second medical device, information derived from at least some of the first clinical information, and
      (c) store the first clinical information locally or in a remote database.

2. The system of claim 1,
   wherein the first medical device is configured to store the first clinical information in the first memory, and the second medical device is configured to store the second clinical information in a second memory, and
   wherein the at least one control module is further configured to establish access by the second medical device to the first memory to enable the handoff of the first clinical information.

3. The system of claim 2, wherein the first memory and the second memory are part of a same memory device.

4. The system of claim 1, wherein the at least one control module is further configured to determine that the first medical device and the second medical device are proximately located in response to exchange of radio frequency signals.

5. The system of claim 1, wherein the at least one control module is further configured to determine that the first medical device and the second medical device are proximately located in response to receipt of a global positioning system (GPS) signal from each of the first medical device and the second medical device.

6. The system of claim 1, wherein the at least one control module is further configured to determine that the first medical device and the second medical device are proximately located in response to each of the first medical device and the second medical device being connected to a shared local area network (LAN).

7. The system of claim 1, wherein the at least one control module is further configured to determine that the first and second medical devices are to be used on the patient during the medical event based on one or more correlations between (a) one or more of the first clinical information, a time for the first clinical information, and an identity of a caregiver for the first clinical information, and (b) one or more of the second clinical information, a time for the second clinical information, and an identity of a caregiver for the second clinical information.

8. The system of claim 2, wherein the first memory is provided on the first medical device and the second memory is provided on the second medical device.

9. The system of claim 2,
wherein at least one of the first memory and the second memory is located remotely from the first and second medical devices in a network, and
wherein the first medical device and the second medical device are communicably coupled via the network, and
wherein the at least one control module is further configured to enable the handoff of the first clinical information via the network.

10. The system of claim 1,
wherein the first medical device and the second medical device are configured to communicatively couple with one another for direct device-to-device communications, and
wherein the at least one control module is further configured to establish the direct device-to-device communications to enable the handoff of the first clinical information.

11. The system of claim 1, wherein the first clinical information details administration of cardiopulmonary resuscitation (CPR) to the patient during the first part of the medical event.

12. The system of claim 1, wherein, in response to the handoff, the second medical device is configured to display chest compression metrics included in or derived from at least some of the first clinical information.

13. The system of claim 6, wherein the handoff of the first clinical information is enabled via the LAN based on authentication of one or both of the first and second medical devices.

14. The system of claim 13, wherein modifying operation of the second medical device based at least in part on the first clinical information comprises modifying one or more algorithms used by the second medical device.

15. The system of claim 14, wherein the one or more algorithms used by the second medical device comprise at least one clinical decision support algorithm.

16. The system of claim 15, wherein modifying operation of the second medical device based at least in part on the first clinical information comprises modifying an output of the second medical device to indicate the handoff of the first clinical information to the second medical device.

17. The system of claim 16, wherein the output of the second medical device comprises one or more of an audio signal and a visual indication on a screen of the second medical device.

18. The system of claim 1, wherein the at least one control module is provided with at least one of the first medical device and the second medical device.

19. The system of claim 1, wherein the at least one control module is provided remotely from the first and second medical devices with a network.

20. The system of claim 7,
wherein the time for the first clinical information is a time stored with the first clinical information, and
wherein the time for the second clinical information is a time of a query sent to the at least one control module by the second medical device.

21. The system of claim 7,
wherein the at least one control module is provided remotely from the first and second medical devices with a network, and
wherein the time for the first clinical information and the time for the second clinical information are communication traffic times for network communication traffic between the first and second medical devices and the at least one control module.

22. The system of claim 1, wherein, in response to the handoff, the second medical device is configured to display one or more visual representations of the first clinical information, the one or more visual representations comprising one or more of:
a visual representation of a presenting heart rhythm of the patient when the first medical device began monitoring the patient,
a visual representation of a heart rhythm of the patient immediately prior to cardiac arrest, and
a visual representation of a heart rhythm of the patient subsequent to an administration of a shock.

23. The system of claim 7, wherein the second patient specific input provided at the second medical device comprises the patient's name.

24. The system of claim 1, wherein, in response to the handoff, the second medical device is configured to modify its operation based at least in part on the first clinical information.

25. The system of claim 1, wherein establishing the communicative coupling further comprises:
generating, by the second medical device, a network identifier for the second medical device using an encryption algorithm and a master key;
generating, by the first medical device, the network identifier for the second medical device using the encryption algorithm and the master key; and
using the generated network identifier to establish the communicative coupling.

* * * * *